(12) United States Patent
Towler et al.

(10) Patent No.: US 7,060,463 B2
(45) Date of Patent: Jun. 13, 2006

(54) **DNA MOLECULES ENCODING *MACACA MULATTA* ANDROGEN RECEPTOR**

(75) Inventors: Dwight A. Towler, Brentwood, MO (US); Fang Chen, North Wales, PA (US)

(73) Assignee: Merck & Co., Inc., Rahway, NJ (US)

(*) Notice: Subject to any disclaimer, the term of this patent is extended or adjusted under 35 U.S.C. 154(b) by 348 days.

(21) Appl. No.: 10/476,724

(22) PCT Filed: May 3, 2002

(86) PCT No.: PCT/US02/14175

§ 371 (c)(1),
(2), (4) Date: Oct. 31, 2003

(87) PCT Pub. No.: WO02/090529

PCT Pub. Date: Nov. 14, 2002

(65) Prior Publication Data

US 2004/0254105 A1    Dec. 16, 2004

Related U.S. Application Data

(60) Provisional application No. 60/289,573, filed on May 8, 2001.

(51) Int. Cl.
*C12N 15/11* (2006.01)
*C12N 5/10* (2006.01)
*C12N 15/63* (2006.01)

(52) U.S. Cl. .................. 435/69.1; 435/320.1; 435/325; 536/23.5

(58) Field of Classification Search .................. None
See application file for complete search history.

(56) References Cited

U.S. PATENT DOCUMENTS 5,614,620 A    3/1997    Liao et al.

FOREIGN PATENT DOCUMENTS

WO    WO 89/09791    10/1989

OTHER PUBLICATIONS

Abdelgadir, et al., "Androgen Receptor Messenger Ribonucleic Acid in Brains and Pituitaries of Male Rhesus Monkeys: Studies on Distribution, Hormonal Control, and . . . ", Bio. of Reprod. 1999, vol. 60, pp. 1251-1256.
Choong, et al., "Evolution of the Primate Androgen Receptor: A Structural Basis for Disease", J. Mol. Evol.1998, vol. 47, No. 3, pp. 334-342.

*Primary Examiner*—Michael Pak
(74) *Attorney, Agent, or Firm*—John David Reilly; Joanne M. Giesser

(57) ABSTRACT

The present invention discloses the isolation and characterization of cDNA molecules encoding novel androgen receptor (AR) protein from *Macaca mulatta*. Also within the scope of the disclosure are recombinant vectors, recombinant host cells, methods of screening for modulators of *Macaca mulatta* AR (rhAR) activity, purified proteins and fusion proteins which comprise all or a portion of the rhAR protein, transgenic mice comprising a transgene encoding the rhAR protein, as well as production of antibodies against AR, or epitopes thereof.

24 Claims, 10 Drawing Sheets

```
CCCAAAAAAT AAAAACAAAC AAAAACAAAA CAAAACAAAA AAAACGAATA
AAGAAAAAGG TAATAACTCA GTTCTTATTT GCACCTACTT CCAGTGGACA
CTGAATTTGG AAGGTGGAGG ATTCTTGTTT TTTCTTTTAA GATCGGGCAT
CTTTTGAATC TACCCCTCAA GTGTTAAGAG ACAGACTGTG AGCCTAGCAG
GGCAGATCTT GTCCACCGTG TGTCTTCTTT TGCAGGAGAC TTTGAGGCTG
TCAGAGCGCT TTTTGCGTGG TTGCTCCCGC AAGTTTCCTT CTCTGGAGCT
TCCCGCAGGT GGGCAGCTAG CTGCAGCGAC TACCGCATCA TCACAGCCTG
TTGAACTCTT CTGAGCAAGA GAAGGGGAGG CGGGGTAAGG GAAGTAGGTG
GAAGATTCAG CCAAGCTCAA GGATGGAGGT GCAGTTAGGG CTGGGGAGGG
TCTACCCTCG GCCGCCGTCC AAGACCTACC GAGGAGCTTT CCAGAATCTG
TTCCAGAGCG TGCGCGAAGT GATCCAGAAC CCGGGCCCCA GGCACCCAGA
GGCCGCGAGC GCAGCACCTC CCGGCGCCAG TTTGCAGCAG CAGCAGCAGC
AGCAGCAAGA AACTAGCCCC CGGCAACAGC AGCAGCAGCA GCAGGGTGAG
GATGGTTCTC CCCAAGCCCA TCGTAGAGGC CCCACAGGCT ACCTGGTCCT
GGATGAGGAA CAGCAGCCTT CACAGCCTCA GTCAGCCCCG GAGTGCCACC
CCGAGAGAGG TTGCGTCCCA GAGCCTGGAG CCGCCGTGGC CGCCGGCAAG
GGGCTGCCGC AGCAGCTGCC AGCACCTCCG GACGAGGATG ACTCAGCTGC
CCCATCCACG TTGTCTCTGC TGGGCCCCAC TTTCCCCGGC TTAAGCAGCT
GCTCCGCCGA CCTTAAAGAC ATCCTGAGCG AGGCCAGCAC CATGCAACTC
CTTCAGCAAC AGCAGCAGGA AGCAGTATCC GAAGGCAGCA GCAGCGGGAG
AGCGAGGGAG GCCTCGGGGG CTCCCACTTC CTCCAAGGAC AATTACTTAG
AGGGCACTTC GACCATTTCT GACAGCGCCA AGGAGCTGTG TAAGGCAGTG
TCGGTGTCCA TGGGCTTGGG TGTGGAGGCG TTGGAGCATC TGAGTCCAGG
GGAACAGCTT CGGGGGGATT GCATGTACGC CCCAGTTTTG GGAGTTCCAC
CCGCTGTGCG TCCCACTCCG TGTGCCCCAT TGGCCGAATG CAAAGGTTCT
```

FIG.1A

```
CTGCTAGACG ACAGCGCAGG CAAGAGCACT GAAGATACTG CTGAGTATTC
CCCTTTCAAG GGAGGTTACA CCAAAGGGCT AGAAGGCGAG AGCCTAGGCT
GCTCTGGCAG CGCTGCAGCA GGGAGCTCCG GGACACTTGA ACTGCCGTCC
ACCCTGTCTC TCTACAAGTC CGGAGCACTG GACGAGGCAG CTGCGTACCA
GAGTCGCGAC TACTACAACT TTCCACTGGC TCTGGCCGGG CCGCCGCCCC
CTCCACCGCC TCCCCATCCC CACGCTCGCA TCAAGCTGGA GAACCCGCTG
GACTATGGCA GCGCCTGGGC GGCTGCGGCG GCGCAGTGCC GCTATGGGGA
CCTGGCGAGC CTGCATGGCG CGGGTGCAGC GGGACCCGGC TCTGGGTCAC
CCTCAGCGGC CGCTTCCTCA TCCTGGCACA CTCTCTTCAC AGCCGAAGAA
GGCCAGTTGT ATGGACCGTG TGGTGGTGGG GGCGGCGGCG GTGGCGGCGG
CGGCGGCGGC GCAGGCGAGG CGGGAGCTGT AGCCCCCTAC GGCTACACTC
GGCCACCTCA GGGGCTGGCG GGCCAGGAAG GCGACTTCAC CGCACCTGAT
GTGTGGTACC CTGGCGGCAT GGTGAGCAGA GTGCCCTATC CCAGTCCCAC
TTGTGTCAAA AGCGAGATGG GCCCCTGGAT GGATAGCTAC TCCGGACCTT
ACGGGGACAT GCGTTTGGAG ACTGCCAGGG ACCATGTTTT GCCAATTGAC
TATTACTTTC CACCCCAGAA GACCTGCCTG ATCTGTGGAG ATGAAGCTTC
TGGGTGTCAC TATGGAGCTC TCACATGTGG AAGCTGCAAG GTCTTCTTCA
AAAGAGCCGC TGAAGGGAAA CAGAAGTACC TGTGTGCCAG CAGAAATGAT
TGCACTATTG ATAAATTCCG AAGGAAAAAT TGTCCATCTT GCCGTCTTCG
GAAATGTTAT GAAGCAGGGA TGACTCTGGG AGCCCGGAAG CTGAAGAAAC
TTGGTAATCT GAAACTACAG GAGGAAGGAG AGGCTTCCAG CACCACCAGC
CCCACTGAGG AGACAGCCCA GAAGCTGACA GTGTCACACA TTGAAGGCTA
TGAATGTCAG CCCATCTTTC TGAATGTCCT GGAGGCCATT GAGCCAGGTG
TGGTGTGTGC TGGACATGAC AACAACCAGC CCGACTCCTT CGCAGCCTTG
CTCTCTAGCC TCAATGAACT GGGAGAGAGA CAGCTTGTAC ATGTGGTCAA
```

FIG.1B

```
GTGGGCCAAG GCCTTGCCTG GCTTCCGCAA CTTACACGTG GACGACCAGA
TGGCTGTCAT TCAGTACTCC TGGATGGGGC TCATGGTGTT TGCCATGGGC
TGGCGATCCT TCACCAATGT CAACTCCAGG ATGCTCTACT TTGCCCCTGA
TCTGGTTTTC AATGAGTACC GCATGCACAA ATCCCGGATG TACAGCCAGT
GTGTCCGAAT GAGGCACCTC TCTCAAGAGT TTGGATGGCT CCAAATCACC
CCCCAGGAAT TCCTGTGCAT GAAAGCGCTG CTACTCTTCA GCATTATTCC
AGTGGATGGG CTGAAAAATC AAAAATTCTT TGATGAACTT CGAATGAACT
ACATCAAGGA ACTCGATCGT ATCATTGCAT GCAAAAGAAA AAATCCCACA
TCCTGCTCAA GGCGTTTCTA CCAGCTCACC AAGCTCCTGG ACTCCGTGCA
GCCTATTGCG AGAGAGCTGC ATCAGTTCAC TTTTGACCTG CTAATCAAGT
CACACATGGT GAGCGTGGAC TTTCCGGAAA TGATGGCAGA GATCATCTCT
GTGCAAGTGC CCAAGATCCT TTCTGGGAAA GTCAAGCCCA TCTATTTCCA
CACCCAGTGA AGCATTGGAA ATCCCTATTT CCTCACCCCA GCTCATGCCC
CCTTTCAGAT GTCTTCTGCC TGTTA (SEQ ID NO:1)
```

FIG. 1C

MEVQLGLGRV YPRPPSKTYR GAFQNLFQSV REVIQNPGPR HPEAASAAPP
GASLQQQQQQ QQETSPRQQQ QQQQGEDGSP QAHRRGPTGY LVLDEEQQPS
QPQSAPECHP ERGCVPEPGA AVAAGKGLPQ QLPAPPDEDD SAAPSTLSLL
GPTFPGLSSC SADLKDILSE ASTMQLLQQQ QQEAVSEGSS SGRAREASGA
PTSSKDNYLE GTSTISDSAK ELCKAVSVSM GLGVEALEHL SPGEQLRGDC
MYAPVLGVPP AVRPTPCAPL AECKGSLLDD SAGKSTEDTA EYSPFKGGYT
KGLEGESLGC SGSAAAGSSG TLELPSTLSL YKSGALDEAA AYQSRDYYNF
PLALAGPPPP PPPPHPHARI KLENPLDYGS AWAAAAAQCR YGDLASLHGA
GAAGPGSGSP SAAASSSWHT LFTAEEGQLY GPCGGGGGGG GGGGGGAGEA
GAVAPYGYTR PPQGLAGQEG DFTAPDVWYP GGMVSRVPYP SPTCVKSEMG
PWMDSYSGPY GDMRLETARD HVLPIDYYFP PQKT<u>CLICGD EASGCHYGAL
TCGSCKVFFK RAAEGKQKYL CASRNDCTID KFRRKNCPSC RLRKCYEAGM</u>
TLGARKLKKL GNLKLQEEGE ASSTTSPTEE TAQKLTVSHI EGYECQPIFL
NVLEAIEPGV VCAGHDNNQP DSFAALLSSL NELGERQLVH VVKWAKALPG
FRNLHVDDQM AVIQYSWMGL MVFAMGWRSF TNVNSRMLYF APDLVFNEYR
MHKSRMYSQC VRMRHLSQEF GWLQITPQEF LCMKALLLFS IIPVDGLKNQ
KFFDELRMNY IKELDRIIAC KRKNPTSCSR RFYQLTKLLD SVQPIARELH
QFTFDLLIKS HMVSVDFPEM MAEIISVQVP KILSGKVKPI YFHTQ (SEQ ID NO:2)

FIG.2

```
CCCAAAAAATAAAAACAAACAAAAACAAAACAAAACAAAAAAAACGAATAAAGAAAAAGG
---------+---------+---------+---------+---------+---------+
GGGTTTTTTATTTTTGTTTGTTTTTGTTTTGTTTTGTTTTTTTTGCTTATTTCTTTTTCC

TAATAACTCAGTTCTTATTTGCACCTACTTCCAGTGGACACTGAATTTGGAAGGTGGAGG
---------+---------+---------+---------+---------+---------+
ATTATTGAGTCAAGAATAAACGTGGCTGAAGGTCACCTGTGACTTAAACCTTCCACCTCC

ATTCTTGTTTTTTCTTTTAAGATCGGGCATCTTTTGAATCTACCCCTCAAGTGTTAAGAG
---------+---------+---------+---------+---------+---------+
TAAGAACAAAAAAGAAAATTCTAGCCCGTAGAAAACTTAGATGGGGAGTTCACAATTCTC

ACAGACTGTGAGCCTAGCAGGGCAGATCTTGTCCACCGTGTGTCTTCTTTTGCAGGAGAC
---------+---------+---------+---------+---------+---------+
TGTCTGACACTCGGATCGTCCCGTCTAGAACAGGTGGCACACAGAAGAAAACGTCCTCTG

TTTGAGGCTGTCAGAGCGCTTTTTGCGTGGTTGCTCCCGCAAGTTTCCTTCTCTGGAGCT
---------+---------+---------+---------+---------+---------+
AAACTCCGACAGTCTCGCGAAAAACGCACCAACGAGGGCGTTCAAAGGAAGAGACCTCGA

TCCCGCAGGTGGGCAGCTAGCTGCAGCGACTACCGCATCATCACAGCCTGTTGAACTCTT
---------+---------+---------+---------+---------+---------+
AGGGCGTCCACCCGTCGATCGACGTCGCTGATGGCGTAGTAGTGTCGGACAACTTGAGAA

CTGAGCAAGAGAAGGGGAGGCGGGGTAAGGGAAGTAGGTGGAAGATTCAGCCAAGCTCAA
---------+---------+---------+---------+---------+---------+
GACTCGTTCTCTTCCCCTCCGCCCCATTCCCTTCATCCACCTTCTAAGTCGGTTCGAGTT

GGATGGAGGTGCAGTTAGGGCTGGGGAGGGTCTACCCTCGGCCGCCGTCCAAGACCTACC
---------+---------+---------+---------+---------+---------+
CCTACCTCCACGTCAATCCCGACCCCTCCCAGATGGGAGCCGGCGGCAGGTTCTGGATGG
  M  E  V  Q  L  G  L  G  R  V  Y  P  R  P  P  S  K  T  Y  R

GAGGAGCTTTCCAGAATCTGTTCCAGAGCGTGCGCGAAGTGATCCAGAACCCGGGCCCCA
---------+---------+---------+---------+---------+---------+
CTCCTCGAAAGGTCTTAGACAAGGTCTCGCACGCGCTTCACTAGGTCTTGGGCCCGGGGT
  G  A  F  Q  N  L  F  Q  S  V  R  E  V  I  Q  N  P  G  P  R

GGCACCCAGAGGCCGCGAGCGCAGCACCTCCCGGCGCCAGTTTGCAGCAGCAGCAGCAGC
---------+---------+---------+---------+---------+---------+
CCGTGGGTCTCCGGCGCTCGCGTCGTGGAGGGCCGCGGTCAAACGTCGTCGTCGTCGTCG
  H  P  E  A  A  S  A  A  P  P  G  A  S  L  Q  Q  Q  Q  Q  Q

AGCAGCAAGAAACTAGCCCCCGGCAACAGCAGCAGCAGCAGCAGGGTGAGGATGGTTCTC
---------+---------+---------+---------+---------+---------+
TCGTCGTTCTTTGATCGGGGGCCGTTGTCGTCGTCGTCGTCGTCCCACTCCTACCAAGAG
  Q  Q  E  T  S  P  R  Q  Q  Q  Q  Q  Q  Q  G  E  D  G  S  P

CCCAAGCCCATCGTAGAGGCCCCACAGGCTACCTGGTCCTGGATGAGGAACAGCAGCCTT
---------+---------+---------+---------+---------+---------+
```

FIG.3A

```
GGGTTCGGGTAGCATCTCCGGGGTGTCCGATGGACCAGGACCTACTCCTTGTCGTCGGAA
  Q   A   H   R   R   G   P   T   G   Y   L   V   L   D   E   E   Q   Q   P   S

CACAGCCTCAGTCAGCCCCGGAGTGCCACCCCGAGAGAGGTTGCGTCCCAGAGCCTGGAG
---------+---------+---------+---------+---------+---------+
GTGTCGGAGTCAGTCGGGGCCTCACGGTGGGGCTCTCTCCAACGCAGGGTCTCGGACCTC
  Q   P   Q   S   A   P   E   C   H   P   E   R   G   C   V   P   E   P   G   A

CCGCCGTGGCCGCCGGCAAGGGGCTGCCGCAGCAGCTGCCAGCACCTCCGGACGAGGATG
---------+---------+---------+---------+---------+---------+
GGCGGCACCGGCGGCCGTTCCCCGACGGCGTCGTCGACGGTCGTGGAGGCCTGCTCCTAC
  A   V   A   A   G   K   G   L   P   Q   Q   L   P   A   P   P   D   E   D   D

ACTCAGCTGCCCCATCCACGTTGTCTCTGCTGGGCCCCACTTTCCCCGGCTTAAGCAGCT
---------+---------+---------+---------+---------+---------+
TGAGTCGACGGGGTAGGTGCAACAGAGACGACCCGGGGTGAAAGGGGCCGAATTCGTCGA
  S   A   A   P   S   T   L   S   L   L   G   P   T   F   P   G   L   S   S   C

GCTCCGCCGACCTTAAAGACATCCTGAGCGAGGCCAGCACCATGCAACTCCTTCAGCAAC
---------+---------+---------+---------+---------+---------+
CGAGGCGGCTGGAATTTCTGTAGGACTCGCTCCGGTCGTGGTACGTTGAGGAAGTCGTTG
  S   A   D   L   K   D   I   L   S   E   A   S   T   M   Q   L   L   Q   Q   Q

AGCAGCAGGAAGCAGTATCCGAAGGCAGCAGCAGCGGGAGAGCGAGGGAGGCCTCGGGGG
---------+---------+---------+---------+---------+---------+
TCGTCGTCCTTCGTCATAGGCTTCCGTCGTCGTCGCCCTCTCGCTCCCTCCGGAGCCCCC
  Q   Q   E   A   V   S   E   G   S   S   S   G   R   A   R   E   A   S   G   A

CTCCCACTTCCTCCAAGGACAATTACTTAGAGGGCACTTCGACCATTTCTGACAGCGCCA
---------+---------+---------+---------+---------+---------+
GAGGGTGAAGGAGGTTCCTGTTAATGAATCTCCCGTGAAGCTGGTAAAGACTGTCGCGGT
  P   T   S   S   K   D   N   Y   L   E   G   T   S   T   I   S   D   S   A   K

AGGAGCTGTGTAAGGCAGTGTCGGTGTCCATGGGCTTGGGTGTGGAGGCGTTGGAGCATC
---------+---------+---------+---------+---------+---------+
TCCTCGACACATTCCGTCACAGCCACAGGTACCCGAACCCACACCTCCGCAACCTCGTAG
  E   L   C   K   A   V   S   V   S   M   G   L   G   V   E   A   L   E   H   L

TGAGTCCAGGGGAACAGCTTCGGGGGGATTGCATGTACGCCCCAGTTTTGGGAGTTCCAC
---------+---------+---------+---------+---------+---------+
ACTCAGGTCCCCTTGTCGAAGCCCCCCTAACGTACATGCGGGGTCAAAACCCTCAAGGTG
  S   P   G   E   Q   L   R   G   D   C   M   Y   A   P   V   L   G   V   P   P

CCGCTGTGCGTCCCACTCCGTGTGCCCCATTGGCCGAATGCAAAGGTTCTCTGCTAGACG
---------+---------+---------+---------+---------+---------+
GGCGACACGCAGGGTGAGGCACACGGGGTAACCGGCTTACGTTTCCAAGAGACGATCTGC
  A   V   R   P   T   P   C   A   P   L   A   E   C   K   G   S   L   L   D   D

ACAGCGCAGGCAAGAGCACTGAAGATACTGCTGAGTATTCCCCTTTCAAGGGAGGTTACA
---------+---------+---------+---------+---------+---------+
```

FIG.3B

```
TGTCGCGTCCGTTCTCGTGACTTCTATGACGACTCATAAGGGGAAAGTTCCCTCCAATGT
  S  A  G  K  S  T  E  D  T  A  E  Y  S  P  F  K  G  G  Y  T

CCAAAGGGCTAGAAGGCGAGAGCCTAGGCTGCTCTGGCAGCGCTGCAGCAGGGAGCTCCG
----------+----------+----------+----------+----------+----------+
GGTTTCCCGATCTTCCGCTCTCGGATCCGACGAGACCGTCGCGACGTCGTCCCTCGAGGC
  K  G  L  E  G  E  S  L  G  C  S  G  S  A  A  A  G  S  S  G

GGACACTTGAACTGCCGTCCACCCTGTCTCTCTACAAGTCCGGAGCACTGGACGAGGCAG
----------+----------+----------+----------+----------+----------+
CCTGTGAACTTGACGGCAGGTGGGACAGAGAGATGTTCAGGCCTCGTGACCTGCTCCGTC
  T  L  E  L  P  S  T  L  S  L  Y  K  S  G  A  L  D  E  A  A

CTGCGTACCAGAGTCGCGACTACTACAACTTTCCACTGGCTCTGGCCGGGCCGCCGCCCC
----------+----------+----------+----------+----------+----------+
GACGCATGGTCTCAGCGCTGATGATGTTGAAAGGTGACCGAGACCGGCCCGGCGGCGGGG
  A  Y  Q  S  R  D  Y  Y  N  F  P  L  A  L  A  G  P  P  P  P

CTCCACCGCCTCCCCATCCCCACGCTCGCATCAAGCTGGAGAACCCGCTGGACTATGGCA
----------+----------+----------+----------+----------+----------+
GAGGTGGCGGAGGGGTAGGGGTGCGAGCGTAGTTCGACCTCTTGGGCGACCTGATACCGT
  P  P  P  P  H  P  H  A  R  I  K  L  E  N  P  L  D  Y  G  S

GCGCCTGGGCGGCTGCGGCGGCGCAGTGCCGCTATGGGGACCTGGCGAGCCTGCATGGCG
----------+----------+----------+----------+----------+----------+
CGCGGACCCGCCGACGCCGCCGCGTCACGGCGATACCCCTGGACCGCTCGGACGTACCGC
  A  W  A  A  A  A  Q  C  R  Y  G  D  L  A  S  L  H  G  A

CGGGTGCAGCGGGACCCGGCTCTGGGTCACCCTCAGCGGCCGCTTCCTCATCCTGGCACA
----------+----------+----------+----------+----------+----------+
GCCCACGTCGCCCTGGGCCGAGACCCAGTGGGAGTCGCCGGCGAAGGAGTAGGACCGTGT
  G  A  A  G  P  G  S  G  S  P  S  A  A  A  S  S  S  W  H  T

CTCTCTTCACAGCCGAAGAAGGCCAGTTGTATGGACCGTGTGGTGGTGGGGGCGGCGGCG
----------+----------+----------+----------+----------+----------+
GAGAGAAGTGTCGGCTTCTTCCGGTCAACATACCTGGCACACCACCACCCCCGCCGCCGC
  L  F  T  A  E  E  G  Q  L  Y  G  P  C  G  G  G  G  G  G

GTGGCGGCGGCGGCGGCGGCGCAGGCGAGGCGGGAGCTGTAGCCCCCTACGGCTACACTC
----------+----------+----------+----------+----------+----------+
CACCGCCGCCGCCGCCGCCGCGTCCGCTCCGCCCTCGACATCGGGGGATGCCGATGTGAG
  G  G  G  G  G  A  G  E  A  G  A  V  A  P  Y  G  Y  T  R

GGCCACCTCAGGGGCTGGCGGGCCAGGAAGGCGACTTCACCGCACCTGATGTGTGGTACC
----------+----------+----------+----------+----------+----------+
CCGGTGGAGTCCCCGACCGCCCGGTCCTTCCGCTGAAGTGGCGTGGACTACACACCATGG
  P  P  Q  G  L  A  G  Q  E  G  D  F  T  A  P  D  V  W  Y  P

CTGGCGGCATGGTGAGCAGAGTGCCCTATCCCAGTCCCACTTGTGTCAAAAGCGAGATGG
----------+----------+----------+----------+----------+----------+
```

FIG.3C

```
GACCGCCGTACCACTCGTCTCACGGGATAGGGTCAGGGTGAACACAGTTTTCGCTCTACC
 G  G  M  V  S  R  V  P  Y  P  S  P  T  C  V  K  S  E  M  G

GCCCCTGGATGGATAGCTACTCCGGACCTTACGGGGACATGCGTTTGGAGACTGCCAGGG
---------+---------+---------+---------+---------+---------+
CGGGGACCTACCTATCGATGAGGCCTGGAATGCCCCTGTACGCAAACCTCTGACGGTCCC
 P  W  M  D  S  Y  S  G  P  Y  G  D  M  R  L  E  T  A  R  D

ACCATGTTTTGCCAATTGACTATTACTTTCCACCCCAGAAGACCTGCCTGATCTGTGGAG
---------+---------+---------+---------+---------+---------+
TGGTACAAAACGGTTAACTGATAATGAAAGGTGGGGTCTTCTGGACGGACTAGACACCTC
 H  V  L  P  I  D  Y  Y  F  P  P  Q  K  T  C  L  I  C  G  D
                                          _____

ATGAAGCTTCTGGGTGTCACTATGGAGCTCTCACATGTGGAAGCTGCAAGGTCTTCTTCA
---------+---------+---------+---------+---------+---------+
TACTTCGAAGACCCACAGTGATACCTCGAGAGTGTACACCTTCGACGTTCCAGAAGAAGT
 E  A  S  G  C  H  Y  G  A  L  T  C  G  S  C  K  V  F  F  K
_____

AAAGAGCCGCTGAAGGGAAACAGAAGTACCTGTGTGCCAGCAGAAATGATTGCACTATTG
---------+---------+---------+---------+---------+---------+
TTTCTCGGCGACTTCCCTTTGTCTTCATGGACACACGGTCGTCTTTACTAACGTGATAAC
 R  A  A  E  G  K  Q  K  Y  L  C  A  S  R  N  D  C  T  I  D
_____

ATAAATTCCGAAGGAAAAATTGTCCATCTTGCCGTCTTCGGAAATGTTATGAAGCAGGGA
---------+---------+---------+---------+---------+---------+
TATTTAAGGCTTCCTTTTTTAACAGGTAGAACGGCAGAAGCCTTTACAATACTTCGTCCCT
 K  F  R  R  K  N  C  P  S  C  R  L  R  K  C  Y  E  A  G  M

TGACTCTGGGAGCCCGGAAGCTGAAGAAACTTGGTAATCTGAAACTACAGGAGGAAGGAG
---------+---------+---------+---------+---------+---------+
ACTGAGACCCTCGGGCCTTCGACTTCTTTGAACCATTAGACTTTGATGTCCTCCTTCCTC
 T  L  G  A  R  K  L  K  K  L  G  N  L  K  L  Q  E  E  G  E

AGGCTTCCAGCACCACCAGCCCCACTGAGGAGACAGCCCAGAAGCTGACAGTGTCACACA
---------+---------+---------+---------+---------+---------+
TCCGAAGGTCGTGGTGGTCGGGGTGACTCCTCTGTCGGGTCTTCGACTGTCACAGTGTGT
 A  S  S  T  T  S  P  T  E  E  T  A  Q  K  L  T  V  S  H  I

TTGAAGGCTATGAATGTCAGCCCATCTTTCTGAATGTCCTGGAGGCCATTGAGCCAGGTG
---------+---------+---------+---------+---------+---------+
AACTTCCGATACTTACAGTCGGGTAGAAAGACTTACAGGACCTCCGGTAACTCGGTCCAC
 E  G  Y  E  C  Q  P  I  F  L  N  V  L  E  A  I  E  P  G  V

TGGTGTGTGCTGGACATGACAACAACCAGCCCGACTCCTTCGCAGCCTTGCTCTCTAGCC
---------+---------+---------+---------+---------+---------+
ACCACACACGACCTGTACTGTTGTTGGTCGGGCTGAGGAAGCGTCGGAACGAGAGATCGG
 V  C  A  G  H  D  N  N  Q  P  D  S  F  A  A  L  L  S  S  L

TCAATGAACTGGGAGAGAGACAGCTTGTACATGTGGTCAAGTGGGCCAAGGCCTTGCCTG
---------+---------+---------+---------+---------+---------+
```

FIG.3D

```
AGTTACTTGACCCTCTCTCTGTCGAACATGTACACCAGTTCACCCGGTTCCGGAACGGAC
  N  E  L  G  E  R  Q  L  V  H  V  V  K  W  A  K  A  L  P  G

GCTTCCGCAACTTACACGTGGACGACCAGATGGCTGTCATTCAGTACTCCTGGATGGGGC
---------+---------+---------+---------+---------+---------+
CGAAGGCGTTGAATGTGCACCTGCTGGTCTACCGACAGTAAGTCATGAGGACCTACCCCG
  F  R  N  L  H  V  D  D  Q  M  A  V  I  Q  Y  S  W  M  G  L

TCATGGTGTTTGCCATGGGCTGGCGATCCTTCACCAATGTCAACTCCAGGATGCTCTACT
---------+---------+---------+---------+---------+---------+
AGTACCACAAACGGTACCCGACCGCTAGGAAGTGGTTACAGTTGAGGTCCTACGAGATGA
  M  V  F  A  M  G  W  R  S  F  T  N  V  N  S  R  M  L  Y  F

TTGCCCCTGATCTGGTTTTCAATGAGTACCGCATGCACAAATCCCGGATGTACAGCCAGT
---------+---------+---------+---------+---------+---------+
AACGGGGACTAGACCAAAAGTTACTCATGGCGTACGTGTTTAGGGCCTACATGTCGGTCA
  A  P  D  L  V  F  N  E  Y  R  M  H  K  S  R  M  Y  S  Q  C

GTGTCCGAATGAGGCACCTCTCTCAAGAGTTTGGATGGCTCCAAATCACCCCCCAGGAAT
---------+---------+---------+---------+---------+---------+
CACAGGCTTACTCCGTGGAGAGAGTTCTCAAACCTACCGAGGTTTAGTGGGGGGTCCTTA
  V  R  M  R  H  L  S  Q  E  F  G  W  L  Q  I  T  P  Q  E  F

TCCTGTGCATGAAAGCGCTGCTACTCTTCAGCATTATTCCAGTGGATGGGCTGAAAAATC
---------+---------+---------+---------+---------+---------+
AGGACACGTACTTTCGCGACGATGAGAAGTCGTAATAAGGTCACCTACCCGACTTTTTAG
  L  C  M  K  A  L  L  L  F  S  I  I  P  V  D  G  L  K  N  Q

AAAAATTCTTTGATGAACTTCGAATGAACTACATCAAGGAACTCGATCGTATCATTGCAT
---------+---------+---------+---------+---------+---------+
TTTTTAAGAAACTACTTGAAGCTTACTTGATGTAGTTCCTTGAGCTAGCATAGTAACGTA
  K  F  F  D  E  L  R  M  N  Y  I  K  E  L  D  R  I  I  A  C

GCAAAAGAAAAAATCCCACATCCTGCTCAAGGCGTTTCTACCAGCTCACCAAGCTCCTGG
---------+---------+---------+---------+---------+---------+
CGTTTTCTTTTTTAGGGTGTAGGACGAGTTCCGCAAAGATGGTCGAGTGGTTCGAGGACC
  K  R  K  N  P  T  S  C  S  R  R  F  Y  Q  L  T  K  L  L  D

ACTCCGTGCAGCCTATTGCGAGAGAGCTGCATCAGTTCACTTTTGACCTGCTAATCAAGT
---------+---------+---------+---------+---------+---------+
TGAGGCACGTCGGATAACGCTCTCTCGACGTAGTCAAGTGAAAACTGGACGATTAGTTCA
  S  V  Q  P  I  A  R  E  L  H  Q  F  T  F  D  L  L  I  K  S

CACACATGGTGAGCGTGGACTTTCCGGAAATGATGGCAGAGATCATCTCTGTGCAAGTGC
---------+---------+---------+---------+---------+---------+
GTGTGTACCACTCGCACCTGAAAGGCCTTTACTACCGTCTCTAGTAGAGACACGTTCACG
  H  M  V  S  V  D  F  P  E  M  M  A  E  I  I  S  V  Q  V  P

CCAAGATCCTTTCTGGGAAAGTCAAGCCCATCTATTTCCACACCCAGTGAAGCATTGGAA
---------+---------+---------+---------+---------+---------+
```

FIG.3E

```
GGTTCTAGGAAAGACCCTTTCAGTTCGGGTAGATAAAGGTGTGGGTCACTTCGTAACCTT
  K  I  L  S  G  K  V  K  P  I  Y  F  H  T  Q

ATCCCTATTTCCTCACCCCAGCTCATGCCCCCTTTCAGATGTCTTCTGCCTGTTA
---------+---------+---------+---------+---------+-----
TAGGGATAAAGGAGTGGGGTCGAGTACGGGGGAAAGTCTACAGAAGACGGACAAT
```

FIG. 3F

DNA MOLECULES ENCODING *MACACA MULATTA* ANDROGEN RECEPTOR

CROSS-REFERENCE TO RELATED APPLICATIONS

The present application claims priority of U.S. provisional application Ser. No. 60/289,573, filed May 8, 2001.

FIELD OF THE INVENTION

The present invention relates in part to isolated nucleic acid molecules (polynucleotides) which encode a *Macaca mulatta* (rhesus monkey) androgen receptor (rhAR) protein. The present invention also relates to recombinant vectors and recombinant hosts which contain a DNA fragment encoding rhAR, substantially purified, biologically active forms of rhAR, including precursor and mature forms of the protein, mutant proteins which retain a biological activity of interest, methods associated with identifying compounds which modulate rhAR activity, and non-human animals which have been subject to intervention to effect rhAR activity.

BACKGROUND OF THE INVENTION

The nuclear receptor superfamily, which includes steroid hormone receptors, are small chemical ligand-inducible transcription factors which have been shown to play roles in controlling development, differentiation and physiological function. Isolation of cDNA clones encoding nuclear receptors reveals several characteristics. First, the $NH_2$-terminal regions, or the A/B domain, which vary in length between receptors, are hypervariable with low homology between family members. There are three internal regions of conservation, referred to as domains C, D and E/F. Region C encodes a cysteine-rich region which is referred to as the DNA binding domain (DBD). Regions D and E/F are within the COOH-terminal section of the protein. Region D encodes the hinge domain which is also referred to as the ligand binding domain (LBD). For a review, see Power et al. (1992, *Trends in Pharmaceutical Sciences* 13: 318–323).

The lipophilic hormones that activate steroid receptors are known to be associated with human diseases. Therefore, the respective nuclear receptors have been identified as possible targets for therapeutic intervention. For a review of the mechanism of action of various steroid hormone receptors, see Tsai and O'Malley (1994, *Annu. Rev. Biochem.* 63: 451–486).

Recent work with non-steroid nuclear receptors has also shown the potential as drug targets for therapeutic intervention. This work reports that peroxisome proliferator activated receptor g (PPARg), identified by a conserved DBD region, promotes adipocyte differentiation upon activation and that thiazolidinediones, a class of antidiabetic drugs, function through PPARg (Tontonoz et al., 1994, *Cell* 79: 1147–1156; Lehmann et al., 1995, *J. Biol. Chem.* 270(22): 12953–12956; Teboul et al., 1995, *J. Biol. Chem.* 270(47): 28183–28187). This indicates that PPARg plays a role in glucose homeostasis and lipid metabolism.

Mangelsdorf et al. (1995, *Cell* 83: 835–839) provide a review of known members of the nuclear receptor superfamily.

U.S. Pat. No. 5,614,620, issued to Liao and Chang on Mar. 25, 1997, discloses nucleotide sequences encoding human and rat androgen receptor, along with the complete amino acid sequence within the open reading frame of the respective androgen receptor.

EP 0 365 657 B1 issued to French et al. Aug. 4, 1999, discloses a recombinant DNA molecule encoding a human androgen receptor, along with the amino acid sequences of human androgen receptor protein.

Choong et al. (1998, *J. Mol. Evol.* 47: 334–342) disclose amino acid sequences for non-human primates such as chimpanzee, baboon, lemur and *Macaca fascicularis* (see SEQ ID NO:6 for nucleotide sequence, see also Gen Bank Accession No. U94179 for the nucleotide and amino acid sequence of *Macaca fascicularis* androgen receptor).

Abdelgadir et al. (1999, *Biology of Reproduction* 60:1251–1256) disclose a PCR fragment representing a 5' portion of the *Macaca mulatta* coding region (see also Gen Bank Accession No. AF092930).

It would be advantageous to identify additional genes closely related to the human androgen receptor gene, such as those possessed by nonhuman primates used for pharmacological investigation, which encode an androgen receptor protein. Since the androgen receptor plays an important role in regulating development, reproduction, and maintenance of bone and muscle, such genes, and their expressed functional proteins, will be useful in assays to select for compounds which modulate the biological activity of the androgen receptor, especially as this modulation pertains to bone formation. The present invention addresses and meets these needs by disclosing isolated nucleic acid molecules which encode a full-length *Macaca mullata* androgen receptor.

SUMMARY OF THE INVENTION

The present invention relates in part to isolated nucleic acid molecules (polynucleotides) which encode a full length *Macaca mulatta* androgen receptor (rhAR), and the use of the expressed rhAR or portion thereof in the identification of androgen selective compounds active in bone formation. The isolated polynucleotides of the present invention encode a non-human primate member of this nuclear receptor superfamily. The DNA molecules disclosed herein may be transfected into a host cell of choice wherein the recombinant host cell provides a source for substantial levels of an expressed functional rhAR. Such a functional nuclear receptor will provide for an effective target for use in screening methodology to identify modulators of the androgen receptor, modulators which may be effective in regulating development, reproduction and maintenance of bone and muscle.

A preferred embodiment of the present invention is disclosed in FIG. 1A–C and SEQ ID NO: 1, an isolated DNA molecule encoding rhAR. Nucleotide 1051 is polymorphic, present as either a 'A' nucleotide or a 'G' nucleotide (see SEQ ID NO:3).

To this end, another preferred embodiment of the present invention is an isolated DNA molecule as shown in FIG. 1A–C and SEQ ID NO:1, except nucleotide 1051 is a 'G' nucleotide instead of a 'A' nucleotide; this isolated DNA molecule being additionally disclosed as SEQ ID NO:3.

The present invention also relates to isolated nucleic acid fragments which encode mRNA expressing a biologically active rhesus monkey androgen receptor which belongs to the nuclear receptor superfamily. A preferred embodiment relates to isolated nucleic acid fragments of SEQ ID NOs:1, and 3 which encode mRNA expressing a biologically functional derivative of rhAR, especially such nucleic acid fragments which encode all or a portion of the LBD and/or DBD regions of the rhAR open reading frame.

The present invention also relates to recombinant vectors and recombinant hosts, both prokaryotic and eukaryotic, transfected and/or transformed to contain the substantially purified nucleic acid molecules disclosed throughout this specification.

A preferred aspect of the present invention relates to a substantially purified form of the novel nuclear trans-acting receptor protein, a rhesus androgen receptor protein, which is disclosed in FIG. 2 (SEQ ID NO:2) as well as allelic variants of the protein disclosed in SEQ ID NO:2. One allelic variant is disclosed herein as SEQ ID NO:4. The Glu-210 residue of rhAR of SEQ ID NO:2 the parental allele. A single nucleotide change at nucleotide 1051 from 'A' (of SEQ ID NO:1) to 'G' (of SEQ ID NO:3) results in an amino acid change at residue 210 of the rhAR, from the Glu residue of SEQ ID NO:2 to a Gly-210 residue as disclosed in SEQ ID NO:4 as the allelic variant.

Another preferred aspect of the present invention relates to a substantially purified, fully processed (including any proteolytic processing, glycosylation and/or phosphorylation) mature rhAR protein obtained from a recombinant host cell containing a DNA expression vector comprising a nucleotide sequence as set forth in SEQ ID NOs: 1 and 3, or nucleic acid fragments thereof as described above, such DNA expression vectors expressing the respective rhAR protein or rhAR precursor protein. It is especially preferred that the recombinant host cell be a eukaryotic host cell, including but not limited to a mammalian cell line, insect cell line, or yeast.

The present invention also relates to biologically functional derivatives of rhAR as set forth as SEQ ID NOs:2 and 4, including but not limited to rhAR mutants and biologically active fragments such as amino acid substitutions, deletions, additions, amino terminal truncations and carboxy-terminal truncations, such that these fragments provide for proteins or protein fragments of diagnostic, therapeutic or prophylactic use and would be useful for screening for agonists and/or antagonists of rhAR function.

The present invention also relates to a non-human transgenic animal which is useful for studying the ability of a variety of compounds to act as modulators of rhAR, or any alternative functional rhAR in vivo by providing cells for culture, in vitro. In reference to the transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as one or a combination of the cDNA clones described herein. The gene and/or transgene may also include genetic regulatory elements and/or structural elements known in the art. A type of target cell for transgene introduction is the embryonic stem cell (ES). ES cells can be obtained from pre-implantation embryos cultured in vitro and fused with embryos (Evans et al., 1981, Nature 292:154–156; Bradley et al., 1984, *Nature* 309:255–258; Gossler et al., 1986, *Proc. Natl. Acad. Sci.* USA 83:9065–9069; and Robertson et al., 1986 *Nature* 322:445–448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468–1474). It will also be within the purview of the skilled artisan to produce transgenic or knock-out invertebrate animals (e.g., C. elegans) which express the rhAR transgene in a wild type background as well in C. elegans mutants knocked out for one or both of the rhAR subunits. These organisms will be helpful in further determining the dominant negative effect of rhAR as well as selecting from compounds which modulate this effect.

The present invention also relates to a non-human transgenic animal which is heterozygous for a functional rhAR gene native to that animal. As used herein, functional is used to describe a gene or protein that, when present in a cell or in vitro system, performs normally as if in a native or unaltered condition or environment. The animal of this aspect of the invention is useful for the study of the specific expression or activity of rhAR in an animal having only one functional copy of the gene. The animal is also useful for studying the ability of a variety of compounds to act as modulators of rhAR activity or expression in vivo or, by providing cells for culture, in vitro. It is reiterated that as used herein, a modulator is a compound that causes a change in the expression or activity of rhAR, or causes a change in the effect of the interaction of rhAR with its ligand(s), or other protein(s). In an embodiment of this aspect, the animal is used in a method for the preparation of a further animal which lacks a functional native AR gene. In another embodiment, the animal of this aspect is used in a method to prepare an animal which expresses the non-native rhAR gene in the absence of the expression of a native AR gene. In particular embodiments the non-human animal is a mouse.

In reference to the transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as rhAR. The gene and/or transgene may also include genetic regulatory elements and/or structural elements known in the art.

An aspect of this invention is a method of producing transgenic animals having a transgene including the non-native rhAR gene on a native AR null background. The method includes providing transgenic animals of this invention whose cells are heterozygous for a native gene encoding a functional rhAR protein and an altered native AR gene. These animals are crossed with transgenic animals of this invention that are hemizygous for a transgene including a non-native rhAR gene to obtain animals that are both heterozygous for an altered native AR gene and hemizygous for a non-native rhAR gene. The latter animals are interbred to obtain animals that are homozygous or hemizygous for the non-native rhAR and are homozygous for the altered native AR gene. In particular embodiments, cell lines are produced from any of the animals produced in the steps of the method.

The transgenic animals of this invention are also useful in studying the tissue and temporal specific expression patterns of a non-native rhAR throughout the animals. The animals are also useful in determining the ability for various forms of wild-type and mutant alleles of a non-native rhAR to rescue the native AR null deficiency. The animals are also useful for identifying and studying the ability of a variety of compounds to act as modulators of the expression or activity of a non-native rhAR in vivo, or by providing cells for culture, for in vitro studies.

Of particular interest are transgenic mice with rhAR where rhAR expression dominates mouse endogenous AR and can be turned on tissue specifically.

As used herein, a "targeted gene" or "Knockout" (KO) is a DNA sequence introduced into the germline of a non-human animal by way of human intervention, including but not limited to, the methods described herein. The targeted genes of the invention include nucleic acid sequences which are designed to specifically alter cognate endogenous alleles. An altered AR gene should not fully encode the same AR as native to the host animal, and its expression product can be altered to a minor or great degree, or absent altogether. In cases where it is useful to express a non-native rhAR gene in a transgenic animal in the absence of a native AR gene we prefer that the altered AR gene induce a null lethal knockout phenotype in the animal. However a more modestly modified AR gene can also be useful and is within the scope of the present invention.

A type of target cell for transgene introduction is the embryonic stem cell (ES). ES cells can be obtained from pre-implantation embryos cultured in vitro and fused with embryos (Evans et al., 1981, *Nature* 292:154–156; Bradley et al., 1984, *Nature* 309:255–258; Gossler et al., 1986, *Proc. Natl. Acad. Sci.* USA 83:9065–9069; and Robertson et al., 1986 *Nature* 322:445–448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468–1474).

The methods for evaluating the targeted recombination events as well as the resulting knockout mice are readily available and known in the art. Such methods include, but are not limited to DNA (Southern) hybridization to detect the targeted allele, polymerase chain reaction (PCR), polyacrylamide gel electrophoresis (PAGE) and Western blots to detect DNA, RNA and protein.

The present invention also relates to polyclonal and monoclonal antibodies raised in response to rhAR, or a biologically functional derivative thereof. In particular, antibodies to the A/B domain and the hinge domain, (D domain) are preferred. To this end, the DNA molecules, RNA molecules, recombinant protein and antibodies of the present invention may be used to screen and measure levels of rhAR. The recombinant proteins, DNA molecules, RNA molecules and antibodies lend themselves to the formulation of kits suitable for the detection and typing of rhAR.

The present invention also relates assays utilized to identify compounds that modulate rhAR activity. One aspect of this portion of the invention is shown in Example Section 2, an in vitro binding assay using a GST-rhARLBD fusion protein. Other assays are contemplated, including but not limited to using rhAR cDNA clones and/or expressed proteins in co-transfection assays to measure bioactivity of compounds, as well as mammalian two-hybrid assays to test the effect of compounds on $NH_2$— and COOH-terminus interaction of *Macaca mulatta* AR. Such assays are described infra.

It is an object of the present invention to provide an isolated nucleic acid molecule which encodes a novel form of a nuclear receptor protein such as human rhAR, human nuclear receptor protein fragments of full length proteins such as rhAR, and mutants which are derivatives of SEQ ID NOs:2 and 4. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for rhAR function.

Another object of this invention is tissue typing using probes or antibodies of this invention. In a particular embodiment, polynucleotide probes are used to identify tissues expressing rhAR mRNA. In another embodiment, probes or antibodies can be used to identify a type of tissue based on rhAR expression or display of rhAR receptors.

It is a further object of the present invention to provide rhAR proteins or protein fragments encoded by the nucleic acid molecules referred to in the preceding paragraphs, including such rhAR proteins which are expressed within host cells transfected with a DNA expression vector which contains an rhAR nucleotide sequence as disclosed herein.

It is a further object of the present invention to provide recombinant vectors and recombinant host cells which comprise a nucleic acid sequence encoding rhAR or a biological equivalent thereof.

It is an object of the present invention to provide a substantially purified form of rhAR, as set forth in SEQ ID NOs:2 and 4.

It is an object of the present invention to provide for biologically functional derivatives of rhAR, including but not necessarily limited to amino acid substitutions, deletions, additions, amino terminal truncations and carboxy-terminal truncations such that these fragment and/or mutants provide for proteins or protein fragments of diagnostic, therapeutic or prophylactic use.

It is also an object of the present invention to provide for rhAR-based in-frame fusion constructions, methods of expressing these fusion constructions and biological equivalents disclosed herein, related assays, recombinant cells expressing these constructs, the expressed fusion proteins, and agonistic and/or antagonistic compounds identified through the use of DNA molecules encoding these rhAR-based fusion proteins. A preferred fusion construct is one which encodes all or a portion of the LBD and/or DBD regions of the rhAR open reading frame. A preferred fusion protein is one which is expressed from such a construct.

It is also an object of the present invention to provide for assays to identify compounds which modulate rhAR activity.

As used herein, "AR" refers to—androgen receptor—.

As used herein, "rhAR" refers to—*Macaca mulatta* androgen receptor—.

As used herein, "DBD" refers to—DNA binding domain—.

As used herein, "LBD" refers to—ligand binding domain—.

As used herein, "SARM" refers to—selective androgen receptor modulator—.

As used herein, the term "mammalian host" refers to any mammal, including a human being.

As used herein, "R1881" refers to methyltrieneolone, also known as 17b-hydroxy-17-methylestra-4,9,11-trien-3-one, the preparation of which is described in Vellux et al., 1963, *Compt. Rend.* 257: 569 et seq.

BRIEF DESCRIPTION OF THE DRAWINGS

FIG. 1A–C shows the nucleotide sequence (SEQ ID NO: 1) which comprises the open reading frame encoding the rhAR. Underlined nucleotide 1051 ('A') is the site of an allelic variant, which may also be represented by a 'G' residue (as disclosed in SEQ ID NO:3).

FIG. 2 shows the amino acid sequence (SEQ ID NO: 2) of rhAR. The region in bold and underlined (from residue 535 to residue 600 of SEQ ID NO:2) is the DNA binding domain (DBD). Residue 210 (Glu residue also in bold and underlined) is the site of an allelic variant which may also be represented by a Gly residue (as encoded by SEQ ID NO:3 and disclosed herein as SEQ ID NO:4).

FIG. 3A–F shows the coding (SEQ ID NO:1) and anti-coding (SEQ ID NO:5) strands which comprises the open reading frame for the rhesus androgen receptor protein (SEQ ID NO:2). The underlined portion (i.e., from amino acid residue 535 to amino acid residue 600 of SEQ ID NO:2) represents the DBD region of expressed rhAR protein.

DETAILED DESCRIPTION OF THE INVENTION

The present invention relates to the identification and cloning of genes encoding full length *Macaca mulatta* androgen receptor (rhAR) and their use in the identification of tissue selective androgen compounds, including those active in bone formation, myoanabolism, treatment of sarcopenia, relief of post-menopausal symptoms, treatment of benign prostatic hyperplasia, treatment of acne, treatment of hirsutism, treatment of male hypogonadism, prevention and treatment of prostate cancer, management of lipids, treatment of atherosclerosis, prevention and treatment of breast cancer. The androgen receptor is a member of the nuclear receptor superfamily. The superfamily is composed of a group of structurally related receptors but regulated by chemically distinct ligands. The common structure for them is a conserved DNA binding domain (DBD) located in the center of the peptide and a conserved ligand-binding domain (LBD) at the C-terminus. Eight out of the nine non-variant cysteines form two type II zinc fingers which distinguish them from other DNA-binding proteins.

The present invention relates to isolated nucleic acid molecules (polynucleotides) which encode novel *Macaca mulatta* (rhesus monkey) androgen receptor (rhAR). The isolated polynucleotides of the present invention encode a non-primate member of this nuclear receptor superfamily. The DNA molecules disclosed herein may be transfected into a host cell of choice wherein the recombinant host cell provides a source for substantial levels of an expressed, substantially purified, functional recombinant rhAR, which also forms a portion of the present invention. As noted herein, such a functional nuclear receptor will provide for an effective target for use in screening methodology to identify modulators of the androgen receptor, modulators which may be effective in regulating development, reproduction and maintenance of bone and muscle, treatment of prostate disease, regulation of lipid metabolism and hippocampal function. It is also known that abnormal function of AR can cause prostate cancer. Accumulated information has also indicated that androgen deficiency results in various abnormalities of bone metabolism, such as increased bone loss. Androgen therapy has been used widely to treat a variety of disorders in both men and women. However, the development of an androgen modulator with desirable effect (i.e., bone promotion) and less side effect (i.e., aggressive behavior, acne) has not been achieved. Recent progress in hormone replacement therapy has proven the possibility in developing selective androgen receptor modulators (SARMs). *J. of Clinical Endocrinology & Metabolism*, 84(10): 3459 (1999). Therefore, a compound screening system using AR, such as the rhAR disclosed herein, is needed for safe androgen drug development.

A preferred embodiment of the present invention is disclosed in FIG. 1A–C and SEQ ID NO: 1, an isolated DNA molecule encoding rhAR. Nucleotide 1051 is polymorphic, present as either a 'A' nucleotide or a 'G' nucleotide (see SEQ ID NO:3). This embodiment is shown as follows, with 1051-A being bolded and underlined:

```
  1 CCCAAAAAAT  AAAAACAAAC  AAAAACAAAA  CAAAACAAAA  AAAACGAATA  (SEQ ID NO: 1)

51 AAGAAAAAGG  TAATAACTCA  GTTCTTATTT  GCACCTACTT  CCAGTGGACA

101 CTGAATTTGG  AAGGTGGAGG  ATTCTTGTTT  TTTCTTTTAA  GATCGGGCAT

151 CTTTTGAATC  TACCCCTCAA  GTGTTAAGAG  ACAGACTGTG  AGCCTAGCAG

201 GGCAGATCTT  GTCCACCGTG  TGTCTTCTTT  TGCAGGAGAC  TTTGAGGCTG

251 TCAGAGCGCT  TTTTGCGTGG  TTGCTCCCGC  AAGTTTCCTT  CTCTGGAGCT

301 TCCCGCAGGT  GGGCAGCTAG  CTGCAGCGAC  TACCGCATCA  TCACAGCCTG

351 TTGAACTCTT  CTGAGCAAGA  GAAGGGGAGG  CGGGGTAAGG  GAAGTAGGTG

401 GAAGATTCAG  CCAAGCTCAA  GGATGGAGGT  GCAGTTAGGG  CTGGGGACGG

451 TCTACCCTCG  GCCGCCGTCC  AAGACCTACC  GAGGAGCTTT  CCAGAATCTG

501 TTCCAGAGCG  TGCGCGAAGT  GATCCAGAAC  CCGGGCCCCA  GGCACCCAGA

551 GGCCGCGAGC  GCAGCACCTC  CCGGCGCCAG  TTTGCAGCAG  CAGCAGCAGC

601 AGCAGCAAGA  AACTAGCCCC  CGGCAACAGC  AGCAGCAGCA  GCAGGGTGAG

651 GATGGTTCTC  CCCAAGCCCA  TCGTAGAGGC  CCCACAGGCT  ACCTGGTCCT

701 GGATGAGGAA  CAGCAGCCTT  CACAGCCTCA  GTCAGCCCCG  GAGTGCCACC

751 CCGAGAGAGG  TTGCGTCCCA  GAGCCTGGAG  CCGCCGTGGC  CGCCGGCAAG
```

-continued

```
 801 GGGCTGCCGC AGCAGCTGCC AGCACCTCCG GACGAGGATG ACTCAGCTGC

851 CCCATCCACG TTGTCTCTGC TGGGCCCCAC TTTCCCCGGC TTAAGCAGCT

901 GCTCCGCCGA CCTTAAAGAC ATCCTGAGCG AGGCCAGCAC CATGCAACTC

951 CTTCAGCAAC AGCAGCAGGA AGCAGTATCC GAAGGCAGCA GCAGCGGGAG

1001 AGCGAGGGAG GCCTCGGGGG CTCCCACTTC CTCCAAGGAC AATTACTTAG

1051 AGGGCACTTC GACCATTTCT GACAGCGCCA AGGAGCTGTG TAAGGCAGTG

1101 TCGGTGTCCA TGGGCTTGGG TGTGGAGGCG TTGGAGCATC TGAGTCCAGG

1151 GGAACAGCTT CGGGGGGATT GCATGTACGC CCCAGTTTTG GGAGTTCCAC

1201 CCGCTGTGCG TCCCACTCCG TGTGCCCCAT TGGCCGAATG CAAAGGTTCT

1251 CTGCTAGACG ACAGCGCAGG CAAGAGCACT GAAGATACTG CTGAGTATTC

1301 CCCTTTCAAG GGAGGTTACA CCAAAGGGCT AGAAGGCGAG AGCCTAGGCT

1351 GCTCTGGCAG CGCTGCAGCA GGGAGCTCCG GGACACTTGA ACTGCCGTCC

1401 ACCCTGTCTC TCTACAAGTC CGGAGCACTG GACGAGGCAG CTGCGTACCA

1451 GAGTCGCGAC TACTACAACT TTCCACTGGC TCTGGCCGGG CCGCCGCCCC

1501 CTCCACCGCC TCCCCATCCC CACGCTCGCA TCAAGCTGGA GAACCCGCTG

1551 GACTATGGCA GCGCCTGGGC GGCTGCGGCG GCGCAGTGCC GCTATGGGGA

1601 CCTGGCGAGC CTGCATGGCG CGGGTGCAGC GGGACCCGGC TCTGGGTCAC

1651 CCTCAGCGGC CGCTTCCTCA TCCTGGCACA CTCTCTTCAC AGCCGAAGAA

1701 GGCCAGTTGT ATGGACCGTG TGGTGGTGGG GGCGGCGGCG GTGGCGGCGG

1751 CGGCGGCGGC GCAGGCGAGG CGGGAGCTGT AGCCCCCTAC GGCTACACTC

1801 GGCCACCTCA GGGGCTGGCG GGCCAGGAAG GCGACTTCAC CGCACCTGAT.

1851 GTGTGGTACC CTGGCGGCAT GGTGAGCAGA GTGCCCTATC CCAGTCCCAC

1901 TTGTGTCAAA AGCGAGATGG GCCCCTGGAT GGATAGCTAC TCCGGACCTT

1951 ACGGGGACAT GCGTTTGGAG ACTGCCAGGG ACCATGTTTT GCCAATTGAC

2001 TATTACTTTC CACCCCAGAA GACCTGCCTG ATCTGTGGAG ATGAAGCTTC

2051 TGGGTGTCAC TATGGAGCTC TCACATGTGG AAGCTGCAAG GTCTTCTTCA

2101 AAAGAGCCGC TGAAGGGAAA CAGAAGTACC TGTGTGCCAG CAGAAATGAT

2151 TGCACTATTG ATAAATTCCG AAGGAAAAAT TGTCCATCTT GCCGTCTTCG

2201 GAAATGTTAT GAAGCAGGGA TGACTCTGGG AGCCCGGAAG CTGAAGAAAC

2251 TTGGTAATCT GAAACTACAG GAGGAAGGAG AGGCTTCCAG CACCACCAGC

2301 CCCACTGAGG AGACAGCCCA GAAGCTGACA GTGTCACACA TTGAAGGCTA

2351 TGAATGTCAG CCCATCTTTC TGAATGTCCT GGAGGCCATT GAGCCAGGTG

2401 TGGTGTGTGC TGGACATGAC AACAACCAGC CCGACTCCTT CGCAGCCTTG

2451 CTCTCTAGCC TCAATGAACT GGGAGAGAGA CAGCTTGTAC ATGTGGTCAA

2501 GTGGGCCAAG GCCTTGCCTG GCTTCCGCAA CTTACACGTG GACGACCAGA

2551 TGGCTGTCAT TCAGTACTCC TGGATGGGGC TCATGGTGTT TGCCATGGGC
```

-continued

```
2601 TGGCGATCCT TCACCAATGT CAACTCCAGG ATGCTCTACT TTGCCCCTGA
2651 TCTGGTTTTC AATGAGTACC GCATGCACAA ATCCCGGATG TACAGCCAGT
2701 GTGTCCGAAT GAGGCACCTC TCTCAAGAGT TTGGATGGCT CCAAATCACC
2751 CCCCAGGAAT TCCTGTGCAT GAAAGCGCTG CTACTCTTCA GCATTATTCC
2801 AGTGGATGGG CTGAAAAATC AAAAATTCTT TGATGAACTT CGAATGAACT
2851 ACATCAAGGA ACTCGATCGT ATCATTGCAT GCAAAAGAAA AAATCCCACA
2901 TCCTGCTCAA GGCGTTTCTA CCAGCTCACC AAGCTCCTGG ACTCCGTGCA
2951 GCCTATTGCG AGAGAGCTGC ATCAGTTCAC TTTTGACCTG CTAATCAAGT
3001 CACACATGGT GAGCGTGGAC TTTCCGGAAA TGATGGCAGA GATCATCTCT
3051 GTGCAAGTGC CCAAGATCCT TTCTGGGAAA GTCAAGCCCA TCTATTTCCA
3101 CACCCAGTGA AGCATTGGAA ATCCCTATTT CCTCACCCCA GCTCATGCCC
3151 CCTTTCAGAT GTCTTCTGCC TGTTA.
```

As noted above, nucleotide 1051 represents a single nucleotide polymorphism (SNP). To this end, another preferred embodiment of the present invention is an isolated DNA molecule as shown in FIG. 1A–C and SEQ ID NO:1, except nucleotide 1051 is a 'G' nucleotide instead of a 'A' nucleotide, this isolated DNA molecule being additionally disclosed as SEQ ID NO:3, as follows, with 1051-G being bolded and underlined:

```
   1 CCCAAAAAAT AAAAACAAAC AAAAACAAAA CAAAACAAAA AAAACGAATA  (SEQ ID NO: 3)
  51 AAGAAAAAGG TAATAACTCA GTTCTTATTT GCACCTACTT CCAGTGGACA
 101 CTGAATTTGG AAGGTGGAGG ATTCTTGTTT TTTCTTTTAA GATCGGGCAT
 151 CTTTTGAATC TACCCCTCAA GTGTTAAGAG ACAGACTGTG AGCCTAGCAG
 201 GGCAGATCTT GTCCACCGTG TGTCTTCTTT TGCAGGAGAC TTTGAGGCTG
 251 TCAGAGCGCT TTTTGCGTGG TTGCTCCCGC AAGTTTCCTT CTCTGGAGCT
 301 TCCCGCAGGT GGGCAGCTAG CTGCAGCGAC TACCGCATCA TCACAGCCTG
 351 TTGAACTCTT CTGAGCAAGA GAAGGGGAGG CGGGGTAAGG GAAGTAGGTG
 401 GAAGATTCAG CCAAGCTCAA GGATGGAGGT GCAGTTAGGG CTGGGGAGGG
 451 TCTACCCTCG CCCGCCGTCC AAGACCTACC GAGGAGCTTT CCAGAATCTG
 501 TTCCAGAGCG TGCGCGAAGT GATCCAGAAC CCGGGCCCCA GGCACCCAGA
 551 GGCCGCGAGC GCAGCACCTC CCGGCGCCAG TTTGCAGCAG CAGCAGCAGC
 601 AGCAGCAAGA AACTAGCCCC CGGCAACAGC AGCAGCAGCA GCAGGGTGAG
 651 GATGGTTCTC CCCAAGCCCA TCGTAGAGGC CCCACAGGCT ACCTGGTCCT
 701 GGATGAGGAA CAGCAGCCTT CACAGCCTCA GTCAGCCCCG GAGTGCCACC
 751 CCGAGAGAGG TTGCGTCCCA GAGCCTGGAG CCGCCGTGGC CGCCGGCAAG
 801 GGGCTGCCGC AGCAGCTGCC AGCACCTCCG GACGAGGATG ACTCAGCTGC
 851 CCCATCCACG TTGTCTCTGC TGGGCCCCAC TTTCCCCGGC TTAAGCAGCT
 901 GCTCCGCCGA CCTTAAAGAC ATCCTGAGCG AGGCCAGCAC CATGCAACTC
 951 CTTCAGCAAC AGCAGCAGGA AGCAGTATCC GAAGGGAGGA GCAGCGGGAG
1001 AGCGAGGGAG GCCTCGGGGG CTCCCACTTC CTCCAAGGAC AATTACTTAG
1051 GGGGCACTTC GACCATTTCT GACAGCGCCA AGGAGCTGTG TAAGGCAGTG
1101 TCGGTGTCCA TGGGCTTGGG TGTGGAGGCG TTGGAGCATC TGAGTCCAGG
```

-continued

```
1151 GGAACAGCTT CGGGGGGATT GCATGTACGC CCCAGTTTTG GGAGTTCCAC

1201 CCGCTGTGCG TCCCACTCCG TGTGCCCCAT TGGCCGAATG CAAAGGTTCT

1251 CTGCTAGACG ACAGCGCAGG CAAGAGCACT GAAGATACTG CTGAGTATTC

1301 CCCTTTCAAG GGAGGTTACA CCAAAGGGCT AGAAGGCGAG AGCCTACGCT

1351 GCTCTGGCAG CGCTGCAGCA GGGAGCTCCG GGACACTTGA ACTGCCGTCC

1401 ACCCTGTCTC TCTACAAGTC CGGAGCACTG GACGAGGCAG CTGCGTACCA

1451 GAGTCGCGAC TACTACAACT TTCCACTGGC TCTGGCCGGG CCGCCGCCCC

1501 CTCCACCGCC TCCCCATCCC CACGCTCGCA TCAAGCTGGA GAACCCGCTG

1551 GACTATGGCA GCGCCTGGGC GGCTGCGGCG GCGCAGTGCC GCTATGGGGA

1601 CCTGGCGAGC CTGCATGGCG CGGGTGCAGC GGGACCCGGC TCTGGGTCAC

1651 CCTCAGCGGC CGCTTCCTCA TCCTGGCACA CTCTCTTCAC AGCCGAAGAA

1701 GGCCAGTTGT ATGGACCGTG TGGTGGTGGG GGCGGCGGCG GTGGCGGCGG

1751 CGGCGGCGGC GCAGGCGAGG CGGGAGCTGT AGCCCCCTAC GGCTACACTC

1801 GGCCACCTCA GGGGCTGGCG GGCCAGGAAG GCGACTTCAC CGCACCTGAT

1851 GTGTGGTACC CTGGCGGCAT GGTGAGCAGA GTGCCCTATC CCAGTCCCAC

1901 TTGTGTCAAA AGCGAGATGG GCCCCTGGAT GGATAGCTAC TCCGGACCTT

1951 ACGGGGACAT GCGTTTGGAG ACTGCCAGGG ACCATGTTTT GCCAATTGAC

2001 TATTACTTTC CACCCCAGAA GACCTGCCTG ATCTGTGGAG ATGAAGCTTC

2051 TGGGTGTCAC TATGGAGCTC TCACATGTGG AAGCTGCAAG GTCTTCTTCA

2101 AAAGAGCCGC TGAAGGGAAA CAGAAGTACC TGTGTGCCAG CAGAAATGAT

2151 TGCACTATTG ATAAATTCCG AAGGAAAAAT TGTCCATCTT GCCGTCTTCG

2201 GAAATGTTAT GAAGCAGGGA TGACTCTGGG AGCCCGGAAG CTGAAGAAAC

2251 TTGGTAATCT GAAACTACAG GAGGAAGGAG AGGCTTCCAG CACCACCAGC

2301 CCCACTGAGG AGACAGCCCA GAAGCTGACA GTGTCACACA TTGAAGGCTA

2351 TGAATGTCAG CCCATCTTTC TGAATGTCCT GGAGGCCATT GAGCCAGGTG

2401 TGGTGTGTGC TGGACATGAC AACAACCAGC CCGACTCCTT CGCAGCCTTG

2451 CTCTCTAGCC TCAATGAACT GGGAGAGAGA CAGCTTGTAC ATGTGGTCAA

2501 GTGGGCCAAG GCCTTGCCTG GCTTCCGCAA CTTACACGTG GACGACCAGA

2551 TGGCTGTCAT TCAGTACTCC TGGATGGGGC TCATGGTGTT TGCCATGGGC

2601 TGGCGATCCT TCACCAATGT CAACTCCAGG ATGCTCTACT TTGCCCCTGA

2651 TCTGGTTTTC AATGAGTACC GCATGCACAA ATCCCGGATG TACAGCCAGT

2701 GTGTCCGAAT GAGGCACCTC TCTCAAGAGT TTGGATGGCT CCAAATCACC

2751 CCCCAGGAAT TCCTGTGCAT GAAAGCGCTG CTACTCTTCA GCATTATTCC

2801 AGTGGATGGG CTGAAAAATC AAAAATTCTT TGATGAACTT CGAATGAACT

2851 ACATCAAGGA ACTCGATCGT ATCATTGCAT GCAAAAGAAA AAATCCCACA

2901 TCCTGCTCAA GGCGTTTCTA CCAGCTCACC AAGCTCCTGG ACTCCGTGCA
```

```
-continued
2951 GCCTATTGCG AGAGAGCTGC ATCAGTTCAC TTTTGACCTG CTAATCAAGT

3001 CACACATGGT GAGCGTGGAC TTTCCGGAAA TGATGGCAGA GATCATCTCT

3051 GTGCAAGTGC CCAAGATCCT TTCTGGGAAA GTCAAGCCCA TCTATTTCCA

3101 CACCCAGTGA AGCATTGGAA ATCCCTATTT CCTCACCCCA GCTCATGCCC

3151 CCTTTCAGAT GTCTTCTGCC TGTTA.
```

The above-exemplified isolated DNA molecules, comprise the following characteristics:

(SEQ ID NO: 1)—3175 nuc.: initiating Met (nuc. 423–425) and "TCA" term. codon (nuc. 3106–3108), with a polymorphic site at nucleotide 1051 ('A'), the open reading frame resulting in an expressed protein of 895 amino acids, as set forth in SEQ ID NO:2, with amino acid residue 210 being a Glu (E) residue.

(SEQ ID NO:3)—3175 nuc.: initiating Met (nuc. 423–425) and "TCA" term. codon (nuc.3106–3108), with a polymorphic site at nucleotide 1051 ('G'), the open reading frame resulting in an expressed protein of 895 amino acids, as set forth in SEQ ID NO:4, with amino acid residue 210 being a Gly (G) residue.

The present invention also relates to isolated nucleic acid fragments which encode mRNA expressing a biologically active rhesus monkey androgen receptor which belongs to the nuclear receptor superfamily. A preferred embodiment relates to isolated nucleic acid fragments of SEQ ID NOs:1 and 3 which encode mRNA expressing a biologically functional derivative of rhAR. Any such nucleic acid fragment will encode either a protein or protein fragment comprising at least an intracellular DNA-binding domain and/or ligand binding domain, domains conserved throughout the rhAR nuclear receptor family domain which exist in rhAR (SEQ ID NOs: 2 and 4). Any such polynucleotide includes but is not necessarily limited to nucleotide substitutions (including but not limited to SNPs, such as single nucleotide substitutions as disclosed herein, as well as deletion and/or insertions which fall within the known working definition of a SNP), deletions, additions, amino-terminal truncations and carboxy-terminal truncations such that these mutations encode mRNA which express a protein or protein fragment of diagnostic, therapeutic or prophylactic use and would be useful for screening for agonists and/or antagonists of rhAR.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA). The preferred template is DNA.

It is known that there is a substantial amount of redundancy in the various codons which code for specific amino acids. Therefore, this invention is also directed to those DNA sequences encode RNA comprising alternative codons that code for the eventual translation of the identical amino acid, as shown below:
A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU.

Therefore, the present invention discloses codon redundancy that may result in differing DNA molecules expressing an identical protein. For purposes of this specification, a sequence bearing one or more replaced codons will be defined as a degenerate variation. Also included within the scope of this invention are mutations either in the DNA sequence or the translated protein, which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

As used herein, "purified" and "isolated" may be utilized interchangeably to stand for the proposition that the nucleic acid, protein, or respective fragment thereof in question has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in pure quantities so as to afford the opportunity to generate polyclonal antibodies, monoclonal antibodies, amino acid sequencing, and peptide digestion. Therefore, the nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

Any of a variety of procedures may be used to clone rhAR. These methods include, but are not limited to, (1) a RACE PCR cloning technique (Frohman, et al., 1988, *Proc. Natl. Acad. Sci.* USA 85: 8998–9002). 5' and/or 3' RACE may be performed to generate a full length cDNA sequence. This strategy involves using gene-specific oligonucleotide primers for PCR amplification of rhAR cDNA. These gene-specific primers are designed through identification of an expressed sequence tag (EST) nucleotide sequence which has been identified by searching any number of publicly available nucleic acid and protein databases; (2) direct functional expression of the rhAR following the construction of a rhAR-containing cDNA library in an appropriate expression vector system; (3) screening a rhAR-containing cDNA library constructed in a bacteriophage or plasmid shuttle vector with a labeled degenerate oligonucleotide probe designed from the amino acid sequence of the rhAR protein; (4) screening a rhAR-containing cDNA library constructed in a bacteriophage or plasmid shuttle vector with a partial cDNA encoding the rhAR protein. This partial cDNA is obtained by the specific PCR amplification of rhAR DNA fragments through the design of degenerate oligonucleotide primers from the amino acid sequence known for other nuclear receptors which are related to the rhAR protein; (5) screening a rhAR-containing cDNA library constructed in a bacteriophage or plasmid shuttle vector with a partial cDNA encoding the rhAR protein. This strategy may also involve using gene-specific oligonucleotide primers for PCR amplification of rhAR cDNA identified as an EST as described above; or (6) designing 5' and 3' gene specific oligonucleotides using SEQ ID NO:1 or 3 as a template so that either the full-length cDNA may be generated by known PCR techniques, or a portion of the coding region may be generated by these same known PCR techniques to generate and isolate a portion of the coding region to use as a probe to screen one of numerous types of cDNA and/or genomic libraries in order to isolate a full-length version of the nucleotide molecule encoding rhAR.

It is readily apparent to those ordinarily skilled in the art that other types of libraries, as well as libraries constructed from other cell types-or species types, may be useful for isolating a rhAR-encoding DNA or a rhAR homologue. Other types of libraries include, but are not limited to, cDNA libraries derived from other cells or cell lines other than rhAR cells or tissue such as murine cells, rodent cells or any other such vertebrate host which may contain rhAR-encoding DNA. Additionally a rhAR gene and homologues may be isolated by oligonucleotide- or polynucleotide-based hybridization screening of a vertebrate genomic library, including but not limited to, a murine genomic library, a rodent genomic library, as well as concomitant rhAR genomic DNA libraries.

It is readily apparent to those skilled in the art that suitable cDNA libraries may be prepared from cells or cell lines which have rhAR activity. The selection of cells or cell lines for use in preparing a cDNA library to isolate a cDNA encoding rhAR may be done by first measuring cell-associated rhAR activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding rhAR may also be isolated from a suitable genomic DNA library. Construction of genomic DNA libraries can be performed by standard techniques well known in the art. Well known genomic DNA library construction techniques can be found in Sambrook, et al., supra.

In order to clone the rhAR gene by one of the preferred methods, the amino acid sequence or DNA sequence of rhAR or a homologous protein may be necessary. To accomplish this, the rhAR protein or a homologous protein may be purified and partial amino acid sequence determined by automated sequenators or mass spectroscopy. It is not necessary to determine the entire amino acid sequence, but the linear sequence of two regions of 6 to 8 amino acids can be determined for the PCR amplification of a partial rhAR DNA fragment. Once suitable amino acid sequences have been identified, the DNA molecules capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the rhAR sequence but others in the set will be capable of hybridizing to rhAR DNA even in the presence of DNA oligonucleotides with mismatches. The mismatched DNA oligonucleotides may still sufficiently hybridize to the rhAR DNA to permit identification and isolation of rhAR encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1 or 18–20, either for the purpose of isolating overlapping 5' and 3' RACE products for generation of a full-length sequence coding for rhAR, or to isolate a portion of the nucleotide molecule coding for rhAR for use as a probe to screen one or more cDNA- or genomic-based libraries to isolate a full-length molecule encoding rhAR or rhAR-like proteins.

In an exemplified method, the rhAR full-length cDNA of the present invention was isolated by screening template cDNA synthesized from *Macaca mulatta* prostate mRNA. Oligonucleotide primers based on *Macaca fascicularis* AR were synthesized. Template cDNA was synthesized from *Macaca mulatta* prostate mRNA. $NH_2$ portion and COOH-portion primer pairs were used to generate two PCR fragments, which were subcloned, characterized and assembled into a full length DNA sequence (see SEQ ID NOs: 1 and 3). The cloned *Macaca mulatta* AR cDNA has 7 nucleotide differences from *Macaca fascicularis* AR in the coding region which result in two amino acid residues difference (FIG. 4). The two macaque polyQ and polyG sequences are identical to each other, and are in turn shorter than the corresponding human sequences. A single amino acid difference between the macaque and human AR, [Ala-632], is present in the DBD-Hinge-LBD region.

The present invention also relates to recombinant vectors and recombinant hosts, both prokaryotic and eukaryotic, which have been transfected and/or transformed with the nucleic acid molecules disclosed throughout this specification.

The present invention also relates to methods of expressing rhAR and biological equivalents disclosed herein, the expressed, processed form of the protein, assays employing these recombinantly expressed gene products, cells expressing these gene products, and agonistic and/or antagonistic compounds identified through the use of assays utilizing these recombinant forms, including, but not limited to, one or more modulators of rhAR, either through direct contact with the LBD or through direct or indirect contact with a ligand which either interacts with the DBD or with the wild-type transcription complex which the androgen receptor interacts in trans, thereby modulating bone biology, for example.

The present invention relates to methods of expressing rhAR in recombinant systems and of identifying agonists and antagonists of rhAR. The novel rhAR proteins of the present invention are suitable for use in an assay procedure for the identification of compounds which modulate the transactivation activity of mammalian rhAR. Modulating rhAR activity, as described herein includes the inhibition or activation of this soluble transacting factor and therefore includes directly or indirectly affecting the normal regulation of the rhAR activity. Compounds that modulate rhAR include agonists, antagonists and compounds which directly or indirectly affect regulation of rhAR. When screening compounds in order to identify potential pharmaceuticals that specifically interact with a target protein, it is necessary to ensure that the compounds identified are as specific as possible for the target protein. To do this, it may necessary to screen the compounds against as wide an array as possible of proteins that are similar to the target receptor, including species homologous to rhesus androgen receptor. Thus, in order to find compounds that are potential pharmaceuticals that interact with rhAR, it is necessary not only to ensure that the compounds interact with rhAR (the "plus target") and produce the desired pharmacological effect through rhAR, it is also necessary to determine that the compounds do not interact with proteins B, C, D, etc. (the "minus targets"). In general, as part of a screening program, it is important to have as many minus targets as possible (see Hodgson, 1992, *Bio/Technology* 10:973–980, @ 980). rhAR proteins and the DNA molecules encoding this protein may serve this purpose in assays utilizing, for example, other members of the nuclear receptor superfamily.

As used herein, a "biologically functional derivative" of a wild-type rhAR possesses a biological activity that is related to the biological activity of the wild type rhAR. The term "functional derivative" is intended to include the "fragments," "mutants," "variants," "degenerate variants," "analogs" and "homologues" of the wild type rhAR protein. The term "fragment" is meant to refer to any polypeptide subset of wild-type rhAR, including but not necessarily limited to rhAR proteins comprising amino acid substitutions, deletions, additions, amino terminal truncations and/or carboxy-terminal truncations. The term "mutant" is meant to refer a subset of a biologically active fragment that may be substantially similar to the wild-type form but possesses distinguishing biological characteristics. Such altered characteristics include but are in no way limited to altered substrate binding, altered substrate affinity and altered sensitivity to chemical compounds affecting biological activity of the rhAR or a rhAR functional derivative. The term "variant" is meant to refer to a molecule substantially similar in structure and function to either the wild-type protein or to a fragment thereof.

A variety of mammalian expression vectors may be used to express recombinant rhAR in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

Commercially available mammalian expression vectors which may be suitable for recombinant rhAR expression, include but are not limited to, pcDNA3.1 (Invitrogen), pLITMUS28, pLITMUS29, pLITMUS38 and pLITMUS39 (New England Bioloabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSV-neo (ATCC 37198), pSV2-dhfr (ATCC 37146), pUCTag (ATCC 37460), and IZD35 (ATCC 37565).

A variety of bacterial expression vectors may be used to express recombinant rhAR in bacterial cells. Commercially available bacterial expression vectors which may be suitable for recombinant rhAR expression include, but are not limited to pCRII (Invitrogen), pCR2.1 (Invitrogen), pQE (Qiagen), pET11a (Novagen), lambda gt11 (Invitrogen), pKK223-3 (Pharmacia), and pGEX2T (Pharmacia).

A variety of fungal cell expression vectors may be used to express recombinant rhAR in fungal cells. Commercially available fungal cell expression vectors which may be suitable for recombinant rhAR expression include but are not limited to the ESP® yeast expression system, which utilizes S. pombe as the expression host, pYES2 (Invitrogen) and Pichia expression vector (Invitrogen).

A variety of insect cell expression vectors may be used to express recombinant receptor in insect cells. Commercially available insect cell expression vectors which may be suitable for recombinant expression of rhAR include but are not limited to pBlueBacIII and pBlueBacHis2 (Invitrogen), and pAcG2T (Pharmingen).

An expression vector containing DNA encoding a rhAR or rhAR-like protein may be used for expression of rhAR in a recombinant host cell. Recombinant host cells may be prokaryotic or eukaryotic, including but not limited to bacteria such as *E. coli*, fungal cells such as yeast, mammalian cells including but not limited to cell lines of rhAR, bovine, porcine, monkey and rodent origin, and insect cells including but not limited to *Drosophila*- and silkworm-derived cell lines. Cell lines derived from mammalian species which may be suitable and which are commercially available, include but are not limited to, L cells L-M (TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1(ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

The expression vector may be introduced into host cells via any one of a number of techniques including but not limited to transfection, transformation, protoplast fusion, and electroporation. The expression vector-containing cells are individually analyzed to determine whether they produce rhAR protein. Identification of rhAR expressing cells may be done by several means, including but not limited to immunological reactivity with anti-rhAR antibodies, labeled ligand binding and the presence of host cell-associated rhAR activity.

The cloned rhAR cDNA obtained through the methods described above may be recombinantly expressed by molecular cloning into an expression vector (such as pcDNA3.1, pQE, pBlueBacHis2 and pLITMUS28) containing a suitable promoter and other appropriate transcription regulatory elements, and transferred into prokaryotic or eukaryotic host cells to produce recombinant rhAR. Techniques for such manipulations can be found described in Sambrook, et al., supra, are discussed at length in the Example section and are well known and easily available to the artisan of ordinary skill in the art.

Expression of rhAR DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the rhAR cDNA sequence(s) that yields optimal levels of rhAR, cDNA molecules including but not limited to the following can be constructed: a cDNA fragment containing the full-length open reading frame for rhAR as well as various constructs containing portions of the cDNA encoding only specific domains of the protein or rearranged domains of the protein. All constructs can be designed to contain none, all or portions of the 5' and/or 3' untranslated region of a rhAR cDNA. The expression levels and activity of rhAR can be determined following the introduction, both singly and in combination, of these constructs into appropriate host cells. Following determination of the rhAR cDNA cassette yielding optimal expression in transient assays, this rhAR cDNA construct is transferred to a variety of expression vectors (including recombinant viruses), including but not limited to those for mammalian cells, plant cells, insect cells, oocytes, bacteria, and yeast cells.

A preferred aspect of the present invention relates to a substantially purified form of the novel nuclear trans-acting receptor protein, a rhesus androgen receptor protein, which is disclosed in FIG. 2 (SEQ ID NO:2) as well as a polymorph of the protein disclosed in SEQ ID NO:2, disclosed herein as SEQ ID NO:4.

The rhAR protein disclosed in SEQ ID NO:2 is as follows:

```
MEVQLGLGRV  YPRPPSKTYR  GAFQNLFQSV  REVIQNPGPR  HPEAASAAPP  (SEQ ID NO: 2)

GASLQQQQQQ  QQETSPRQQQ  QQQQGEDGSP  QAHRRGPTGY  LVLDEEQQPS

QPQSAPECHP  ERGCVPEPGA  AVAAGKGLPQ  QLPAPPDEDD  SAAPSTLSLL

GPTFPGLSSC  SADLKDILSE  ASTMQLLQQQ  QQEAVSEGSS  SGRAREASGA

PTSSKDNYLE  GTSTISDSAK  ELCKAVSVSM  GLGVEALEHL  SPGEQLRGDC

MYAPVLGVPP  AVRPTPCAPL  AECKGSLLDD  SAGKSTEDTA  EYSPFKGGYT

KGLEGESLGC  SGSAAAGSSG  TLELPSTLSL  YKSGALDEAA  AYQSRDYYNF

PLALAGPPPP  PPPPHPHARI  KLENPLDYGS  AWAAAAAQCR  YGDLASLHGA

GAAGPGSGSP  SAAASSSWHT  LFTAEEGQLY  GPCGGGGGG   GGGGGGAGEA

GAVAPYGYTR  PPQGLAGQEG  DFTAPDVWYP  GGMVSRVPYP  SPTCVKSEMG

PWMDSYSGPY  GDMRLETARD  HVLPIDYYFP  PQKTCLICGD  EASGCHYGAL

TCGSCKVFFK  RAAEGKQKYL  CASRNDCTID  KFRRKNCPSC  RLRKCYEAGM

TLGARKLKKL  GNLKLQEEGE  ASSTTSPTEE  TAQKLTVSHI  EGYECQPIFL

NVLEAIEPGV  VCAGHDNNQP  DSFAALLSSL  NELGERQLVH  VVKWAKALPG

FRNLHVDDQM  AVIQYSWMGL  MVFAMGWRSF  TNVNSRMLYF  APDLVFNEYR

MHKSRMYSQC  VRMRHLSQEF  GWLQITPQEF  LCMKALLLFS  IIPVDGLKNQ

KFFDELRMNY  IKELDRIIAC  KRKNPTSCSR  RFYQLTKLLD  SVQPIARELH

QFTFDLLIKS  HMVSVDFPEM  MAEIISVQVP  KILSGKVKPI  YFHTQ.
```

As noted herein, the Glu-210 residue (underlined and bolded) of rhAR of SEQ ID NO:2 represents an allelic variant at nucleotide 1051 of SEQ ID NO:1. A single nucleotide change at nucleotide 1051 from 'A' to 'G' results in an amino acid change at residue 210 of the rhAR, from the Glu residue of SEQ ID NO:2 to a Gly residue (underlined and bolded), shown below as SEQ ID NO:4:

of the invention includes, but is not limited to, glutathione S-transferase GST-rhAR fusion constructs. These fusion constructs include, but are not limited to, all or a portion of the ligand-binding domain of rhAR, respectively, as an in-frame fusion at the carboxy terminus of the GST gene. The disclosure of SEQ ID NOS: 1 and 3 provide the artisan of ordinary skill the information necessary to construct any

```
MEVQLGLGRV  YPRPPSKTYR  GAFQNLFQSV  REVIQNPGPR  HPEAASAAPP   (SEQ ID NO: 4)

GASLQQQQQQ  QQETSPRQQQ  QQQQGEDGSP  QAHRRGPTGY  LVLDEEQQPS

QPQSAPECHP  ERGCVPEPGA  AVAAGKGLPQ  QLPAPPDEDD  SAAPSTLSLL

GPTFPGLSSC  SADLKDILSE  ASTMQLLQQQ  QQEAVSEGSS  SGRAREASGA

PTSSKDNYLG  GTSTISDSAK  ELCKAVSVSM  GLGVEALEHL  SPGEQLRGDC

MYAPVLGVPP  AVRPTPCAPL  AECKGSLLDD  SAGKSTEDTA  EYSPFKGGYT

KGLEGESLGC  SGSAAAGSSG  TLELPSTLSL  YKSGALDEAA  AYQSRDYYNF

PLALAGPPPP  PPPPHPHARI  KLENPLDYGS  AWAAAAAQCR  YGDLASLHGA

GAAGPGSGSP  SAAASSSWHT  LFTAEEGQLY  GPCGGGGGGG  GGGGGGAGEA

GAVAPYGYTR  PPQGLAGQEG  DFTAPDVWYP  GGMVSRVPYP  SPTCVKSEMG

PWMDSYSGPY  GDMRLETARD  HVLPIDYYFP  PQKTCLICGD  EASGCHYGAL

TCGSCKVFFK  RAAEGKQKYL  CASRNDCTID  KFRRKNCPSC  RLRKCYEAGM

TLGARKLKKL  GNLKLQEEGE  ASSTTSPTEE  TAQKLTVSHI  EGYECQPIFL

NVLEAIEPGV  VCAGHDNNQP  DSFAALLSSL  NELGERQLVH  VVKWAKALPG

FRNLHVDDQM  AVIQYSWMGL  MVFAMGWRSF  TNVNSRMLYF  APDLVFNEYR

MHKSRMYSQC  VRMRHLSQEF  GWLQITPQEF  LCMKALLLFS  IIPVDGLKNQ

KFFDELRMNY  IKELDRIIAC  KRKNPTSCSR  RFYQLTKLLD  SVQPIARELH

QFTFDLLIKS  HMVSVDFPEM  MAEIISVQVP  KILSGKVKPI  YFHTQ.
```

The underlined portions of SEQ ID NOs:2 and 4, from amino acid residue 535 to residue 600, represent the DNA binding domain (DBD) of the rhAR receptor protein. The DBD participates in regulating protein-protein interactions in AR transrepression pathway. Aarnisalo et al., Endocrinology 140(7):3097 (1999). Transcription activation and repression functions of the androgen receptor are differentially influenced by mutations in the DNA-binding domain. In transactivation, AR forms homodimer and binds DNA response element via DBD.

The present invention also relates to a substantially purified, fully processed (including proteolytic processing, such as processing of a natural, hybrid or synthetic signal sequence, glycosylation and/or phosphorylation) mature rhAR protein obtained from a recombinant host cell containing a DNA expression vector comprising a nucleotide sequence as set forth in SEQ ID NOs: 1 and 3, or nucleic acid fragments thereof as described above, such DNA expression vectors expressing the respective rhAR protein or rhAR precursor protein. It is especially preferred that the recombinant host cell be a eukaryotic host cell, including but not limited to a mammalian cell line or an insect cell line. In another embodiment, it is especially preferred that the recombinant host cell be a yeast host cell.

The present invention also relates to isolated nucleic acid molecules which are fusion constructions expressing fusion proteins useful in assays to identify compounds which modulate mammalian AR. A preferred aspect of this portion of the invention includes, but is not limited to, glutathione S-transferase GST-rhAR fusion constructs. These fusion constructs include, but are not limited to, all or a portion of the ligand-binding domain of rhAR, respectively, as an in-frame fusion at the carboxy terminus of the GST gene. The disclosure of SEQ ID NOS: 1 and 3 provide the artisan of ordinary skill the information necessary to construct any such nucleic acid molecule encoding a GST-nuclear receptor fusion protein. Soluble recombinant GST-nuclear receptor fusion proteins may be expressed in various expression systems, including but in now manner limited to a yeast expression system (see Example Section 2), or Spodoptera frugiperda (Sf21) within insect cells (Invitrogen) using a baculovirus expression vector (e.g., Bac-N-Blue DNA from Invitrogen or pAcG2T from Pharmingen). Example Section 2 discloses construction of GST-Flag-rhARLBD (Mr=60 kDa), which is expressed in yeast. This fusion protein is purified by standard techniques and used in a hydoxyapatite binding assay in the presence of labeled R1881 and unlabeled test compounds. After a parallel binding reaction where increasing concentration of unlabeled test compounds are incubated with $^3$H-R1881, a hydroxyapatite slurry is prepared and processed. Unbound ligand is removed and the subsequent hydroxyapatite pellet is washed and ligand bound GST-rhAR is assessed to quantify the amount of radioligand ($^3$H-R1881) bound to the recombinant rhAR fusion protein. Results are compared to known high affinity ligands such as 5-alpha dihydrotestosterone and unlabeled R1881, which exhibit IC50s of ca. 1 nM. See, Asselin and Melancon, 1977, Steroids 30: 591–604; Ghanadian et al., 1977, Urol. Res. 5(4): 169–173.

Other assays are contemplated for the rhAR cDNA clones of the present invention, including but not limited to the use of these clone(s) to set up co-transfection assays to measure bioactivity of compounds, or to set-up mammalian two-hybrid assays to test the effect of compounds on N— and C-terminus interaction of *Macaca mulatta* AR.

For example, the present invention relates to constructs wherein a receptor construct (e.g., containing the rhAR LBD, e.g., Gal4-rhAR-LBD) and a reporter construct (such as SEAP or LacZ) with regulatory sites that respond to increases and decreases in expression of the receptor construct. Therefore, the present invention includes assays by which modulators of rhAR are identified. Methods for identifying agonists and antagonists of other receptors are well known in the art and can be adapted to identify compounds which effect in vivo levels of rhAR. Accordingly, the present invention includes a method for determining whether a substance is a potential modulator of AR levels that comprises:

(a) transfecting or transforming cells with an expression vector encoding rhAR, (such as the LBD of rhAR) also known as the receptor vector;

(b) transfecting or transforming the cells of step (a) with second expression vector, also known as a reporter vector, which comprises an element known to respond to rhAR through protein-protein interactions but bind a non-rhAR protein or a promoter fragment fused upstream of a reporter gene;

(c) allowing the transfected cells to grow for a time sufficient for rhAR to be expressed;

(d) exposing some of the transfected cells expressing rhAR, the "test cells" to a test substance while not exposing control cells to the test substance;

(e) measuring the expression of the reporter gene in both the test cells and control cells.

Of course, "controls" in such assays may take many forms, such as but not limited to the recitation of step (d) above, or possibly the use of cells not transfected with the nucleic acid molecule expressing rhAR (i.e., non-transfected cells), or cells transfected with vector alone, minus the coding region for rhAR. Also, conditions under which step (d) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. This assay may be conducted with crude cell lysate, or with more purified materials. Alternatively, the transrepression assay may be carried out as follows:

(a) provide test cells by transfecting cells with a receptor expression vector that directs the expression of rhAR or a portion thereof (such as the LBD of rhAR) in the cells;

(b) providing test cells by transfecting the cells of step (a) with a second reporter expression vector that directs expression of a reporter gene under control of a regulatory element which is responsive to rhAR via protein-protein interactions or a portion of the rhAR construct;

(c) exposing the test cells to the substance;

(d) measuring expression of the reporter gene;

(e) comparing the amount of expression of the reporter gene in the test cells with the amount of expression of the reporter gene in control cells that have been transfected with a reporter vector of step (b) but not a receptor vector of step (a).

This assay may be conducted with transfected mammalian cell lines using cell-permeable test compounds.

An alternative assay would be one wherein multiple receptor/reporter constructs are transfected into cells such that the general nature of the trans-acting factor can be measured. It is evident that any number of variations known to one of skill in the art may be utilized in order to provide for an assay to measure the effect of a substance on the ability of the nuclear receptor proteins of the present invention to effect transcription of a promoter of interest via protein-protein interactions with heterologous DNA binding proteins.

The present invention includes additional methods for determining whether a substance is capable of binding to rhAR, i.e., whether the substance is a potential agonist or an antagonist of rhAR, where the method comprises:

(a) providing test cells by transfecting cells with an expression vector that directs the expression of rhAR in the cells;

(b) exposing the test cells and control cells to the substance;

(c) measuring the amount of binding of the substance to rhAR;

(d) comparing the amount of binding of the substance to rhAR in the test cells with the amount of binding of the substance to control cells that have not been transfected with rhAR or a portion thereof; wherein if the amount of binding of the substance is greater in the test cells as compared to the control cells, the substance is capable of binding to rhAR. Determining whether the substance is actually an agonist or antagonist can then be accomplished by the use of functional assays such as the transrepression assay as described above.

Test compounds that regulate rhAR function through gene expression may be evaluated employing the method above.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C.

The assays described above can be carried out with cells that have been transiently or stably transfected with rhAR. Transfection is meant to include any method known in the art for introducing rhAR into the test cells. For example, transfection includes calcium phosphate or calcium chloride mediated transfection, lipofection, infection with a retroviral construct containing rhAR, and electroporation. Where binding of the substance or agonist to rhAR is measured, such binding can be measured by employing a labeled substance or agonist. The substance or agonist can be labeled in any convenient manner known to the art, e.g., radioactively, fluorescently, enzymatically.

The rhAR of the present invention may be used to screen for rhAR ligands by assessing transcriptional regulation proceeding via the ligand-bound rhAR-transcription factor protein-protein interactions. Alternatively, the rhAR of the present invention may be employed to screen for rhAR ligands using co-transfection with classical nuclear receptor response elements that bind the rhAR DBD.

The present invention also relates to polyclonal and monoclonal antibodies raised in response to rhAR. Recombinant rhAR protein can be separated from other cellular proteins by use of an immunoaffinity column made with monoclonal or polyclonal antibodies specific for full-length rhAR protein, or polypeptide fragments of rhAR protein. Additionally, polyclonal or monoclonal antibodies may be raised against a synthetic peptide (usually from about 9 to about 25 amino acids in length) from a portion of the protein as disclosed in SEQ ID NO:2 and/or SEQ ID NO:4. Monospecific antibodies to rhAR are purified from mammalian antisera containing antibodies reactive against rhAR or are prepared as monoclonal antibodies reactive with rhAR using the technique of Kohler and Milstein (1975, *Nature* 256: 495–497). Monospecific antibody as used herein is defined as a single antibody species or multiple antibody species with homogenous binding characteristics for rhAR. Homogenous binding as used herein refers to the ability of the antibody species to bind to a specific antigen or epitope, such as those associated with rhAR, as described above. rhAR-specific antibodies are raised by immunizing animals such as mice, rats, guinea pigs, rabbits, goats, horses and the like, with an appropriate concentration of rhAR protein or a synthetic peptide generated from a portion of rhAR with or without an immune adjuvant.

Preimmune serum is collected prior to the first immunization. Each animal receives between about 0.1 mg and about 1000 mg of rhAR protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of rhAR protein or peptide fragment thereof in, preferably, Freund's complete adjuvant at multiple sites, either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of rhAR in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about $-20°$ C.

Monoclonal antibodies (mAb) reactive with rhAR are prepared by immunizing inbred mice, preferably Balb/c, with rhAR protein. The mice are immunized by the IP or SC route with about 1 mg to about 100 mg, preferably about 10 mg, of rhAR protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of rhAR in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1, MPC-11, S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using rhAR as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-rhAR mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of human rhAR in body fluids or tissue and cell extracts.

It is readily apparent to those skilled in the art that the above-described methods for producing monospecific antibodies may be utilized to produce antibodies specific for rhAR peptide fragments, or full-length rhAR.

rhAR antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8.0). The column is washed with water followed by 0.23 M glycine HCl (pH 2.6) to remove any non-conjugated antibody or extraneous protein. The column is then equilibrated in phosphate buffered saline (PBS) (pH 7.3) and the cell culture supernatants or cell extracts containing full-length rhAR or rhAR protein fragments are slowly passed through the column. The column is then washed with phosphate buffered saline until the optical density (A280) falls to background, then the protein is eluted with 0.23 M glycine-HCl (pH 2.6). The purified rhAR protein is then dialyzed against phosphate buffered saline.

Levels of rhAR in host cells are quantified by a variety of techniques including, but not limited to, immunoaffinity and/or ligand affinity techniques. rhAR-specific affinity beads or rhAR-specific antibodies are used to isolate $^{35}$S-methionine labeled or unlabelled rhAR. Labeled rhAR protein is analyzed by SDS-PAGE. Unlabelled rhAR protein is detected by Western blotting, ELISA or RIA assays employing either rhAR protein specific antibodies and/or antiphosphotyrosine antibodies.

Following expression of rhAR in a host cell, rhAR protein may be recovered to provide rhAR protein in active form. Several rhAR protein purification procedures are available and suitable for use. Recombinant rhAR protein may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

The DNA molecules, RNA molecules, recombinant protein and antibodies of the present invention may be used to screen and measure levels of rhAR. The recombinant proteins, DNA molecules, RNA molecules and antibodies lend themselves to the formulation of kits suitable for the detection and typing of rhAR. Such a kit would comprise a compartmentalized carrier suitable to hold in close confinement at least one container. The carrier would further comprise reagents such as recombinant rhAR or anti-rhAR antibodies suitable for detecting rhAR. The carrier may also contain a means for detection such as labeled antigen or enzyme substrates or the like.

Pharmaceutically useful compositions comprising modulators of rhAR may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified rhAR, or either rhAR agonists or antagonists.

Therapeutic or diagnostic compositions comprising modulators of rhAR are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drugs availability to target sites. This involves a consideration of the distribution, equilibrium, and elimination of a drug.

The following examples are provided to illustrate the present invention without, however, limiting the same hereto.

EXAMPLE 1

Isolation and Characterization of a DNA Molecule Encoding rhAR

The DNA sequence for *Macaca fascicularis* monkey AR (Gen Bank Acc. # U94179, also disclosed in the attached sequence listing as SEQ ID NO:6) and an EST for *Macaca mulatta* AR (Gen Bank Accession No. AF092930) may be used for primer designing. The nucleotide sequence for *Macaca mulatta* AR EST is as follows:

```
TCTCAAGAGT  TTGGATGGCT  CCAAATCACC  CCCCAGGAAT  TCCTGTGCAT  (SEQ ID NO: 7)

GAAAGCGCTG  CTACTCTTCA  GCATTATTCC  AGTGGATGGG  CTGAAAAATC

AAAAATTCTT  TGATGAACTT  CGAATGAACT  ACATCAAGGA  ACTCGATCGT

ATCATTGCAT  GCAAAAGAAA  AAATCCCACA  TCCTGCTCAA  GGCGTTTCTA

CCAGCTCACC  AAGCTCCTGG  ACTCCGTGCA  GCCTATTGCG  AGAGAGCTGC

ATCAGTTCAC  TTTTGACCTG  CTAATCAAGT  CACACATGGT  GAGCGTGGAC

TTTCCGGAAA  TGATGGCAGA  GATCATCTC.
```

Messenger RNA from rhesus monkey prostate was prepared and cDNA was synthesized by standard methods. The full-length *Macaca mulatta* AR was cloned via standard PCR methodology. Oligonucleotide primers were based on *Macaca fascicularis* AR. Template cDNA was synthesized from *Macaca mulatta* prostate mRNA. Primer pairs mkARF2 (5'-ATG GAG GTG CAG TTA GGG CTG-3';

SEQ ID NO:8) and mkARR5 (5'-GGT CTT CTG GGG TGG AAA GTA-3'; SEQ ID NO:9) were used to obtain the NH$_2$-terminal portion of the gene via PCR, while the COOH-terminal portion was obtained using mkARF5 (5'-ACG GCT ACA CTC GGC CAC CTC-3'; SEQ ID NO:10) and mkARR2 (5'-AAC AGG CAG AAG ACA TCT GAA-3' SEQ ID NO:11). Each fragment was sub-cloned into a pCRII vector and sequencing verification was performed on DNA from each sub-clones. Clones containing wild type cDNA sequences as compared to the consensus sequence from both NH$_2$— and COOH— terminal DNA sequence assembly were used for full-length cDNA construction. The final full-length cDNA was obtained through ligating the 5' and the 3' end of the cDNA at a KpnI site and cloning into a pCRII vector. The nucleotide sequence was again verified via sequencing. Also, the starting Met and 5'-UTR information for *Macaca mulatta* AR was obtained through cDNA extension on subdivided *Macaca mulatta* cDNA library using mkARR7 primer (5'-GGC GGC CGA GGG TAG ACC CTC-3' SEQ ID NO:12). The cloned *Macaca mulatta* AR cDNA shows seven nucleotide differences from *Macaca fascicularis* AR in the coding region which result in two amino acid residues differences. Both open reading frames show identical polyQ and polyG sequences which are shorter than the human version, with the DBD and LBD regions being identical to the human version.

EXAMPLE 2

Generation of GST-rhAR Fusion Proteins for Use in In Vitro Screening Assays

Expression vector construction: PCR fragment containing residues 601 to 895, which contains the whole LBD, was inserted into pESP-1 expression vector (#251600, Stratagene, Lo Jolla, Calif.) at SmaI site which makes the rhARLBD down stream of GST-Flag tag. The final conjunction sequences are vector 5'-GGA TCC CCC ACT CTG GGA GCC . . . CTG CCT GTT GGG TAA-3' vector.

AR Expression—GST-Flag-rhARLBD (Mr=60 kDa) is expressed in yeast using pESP-1 vector according to Stratagene's protocol and lysed in TEGM/DTT/PI buffer [10 mM Tris, pH7.4, 1 mM EDTA, 10% glycerol, 10 mM molybdate, 2 mM DTT, 50 ul of yeast protease inhibitor cocktail (PI: Sigma) per gram of yeast and 1/10 vol. of PI complete (PI: Boehringer-Mannheim) per gram of yeast.

Fusion Protein Purification—The above fusion protein is purified using anti-flag M2 affinity gel (Sigma) via batch purification method using TEGM/DTT buffer. The protein is eluted using TEGM/DTT buffer containing 100 ug/ml of Flag peptide.

Hydroxyapatite Binding Assay—Typically, 0.25 ug/ml of recombinant purified GST-Flag-rhARLBD and 2 nM $^3$H-R1881 are combined in 100 ul binding reaction (with 50 mM Tris, pH7.5, 10% glycerol, 0.8 M NaCl, 1 mg/ml BSA and 2 mM dithiothreitol) that is incubated for 18 hours at 4° C. $^3$H-R1881 binding displacement is assessed in parallel binding reaction aliquots in the presence of varying concentrations of unlabeled test compounds. Following the initial 18 hour binding reaction, 100 ul of a 50% (wt/vol) hydroxyapatite (HAP) slurry is added to each sample, vortexed, and incubated on ice for ~10 min. The samples are then centrifuged and the supernatant aspirated to remove unbound ligand. The HAP pellet is washed three times with wash buffer (40 mM Tris, pH7.5, 100 mM KCl, 1 mM EDTA and 1 mM EGTA). The 3× washed HAP pellet containing ligand-bound GST-RhAR is transferred in 95% EtOH to a scintillation vial containing 5 ml scintillation fluid, mixed and counted to quantify the amount of radioligand (3H-R1881) bound to the recombinant RhAR fusion protein. Results are compared to known high affinity ligands such as 5-alpha dihydrotestosterone and unlabeled R1881, which exhibit IC50s of ca. 1 nM.

While the foregoing specification teaches the principles of the present invention, with examples provided for the purpose of illustration, it will be understood that the practice of the invention encompasses all of the usual variations, adoptions, or modifications, as come within the scope of the following claims and their equivalents.

SEQUENCE LISTING

```
<160> NUMBER OF SEQ ID NOS: 12

<210> SEQ ID NO 1
<211> LENGTH: 3175
<212> TYPE: DNA
<213> ORGANISM: Macaca mulatta

<400> SEQUENCE: 1
cccaaaaaat aaaaacaaac aaaaacaaaa caaaacaaaa aaaacgaata agaaaaagg      60 taataactca gttcttattt gcacctactt ccagtggaca ctgaatttgg aaggtggagg    120
attcttgttt tttcttttaa gatcgggcat cttttgaatc taccoctcaa gtgttaagag    180 acagactgtg agcctagcag ggcagatctt gtccaccgtg tgtcttcttt tgcaggagac    240
tttgaggctg tcagagcgct ttttgcgtgg ttgctcccgc aagtttcctt ctctggagct    300
tcccgcaggt gggcagctag ctgcagcgac taccgcatca tcacagcctg ttgaactctt    360
ctgagcaaga gaagggagg cggggtaagg gaagtaggtg gaagattcag ccaagctcaa     420
ggatggaggt gcagttaggg ctggggaggg tctaccctcg gccgccgtcc aagacctacc    480
```

-continued

```
gaggagcttt ccagaatctg ttccagagcg tgcgcgaagt gatccagaac ccgggcccca    540
ggcacccaga ggccgcgagc gcagcacctc ccggcgccag tttgcagcag cagcagcagc    600
agcagcaaga aactagcccc cggcaacagc agcagcagca gcaggtgag  gatggttctc    660 cccaagccca tcgtagaggc cccacaggct acctggtcct ggatgaggaa cagcagcctt    720
cacagcctca gtcagcccg  gagtgccacc ccgagagagt tgcgtccca  gagcctggag    780 ccgccgtggc cgccggcaag gggctgccgc agcagctgcc agcacctccg gacgaggatg    840
actcagctgc cccatccacg ttgtctctgc tgggccccac tttccccggc ttaagcagct    900
gctccgccga ccttaaagac atcctgagcg aggccagcac catgcaactc cttcagcaac    960
agcagcagga agcagtatcc gaaggcagca gcagcgggag agcgagggag gcctcggggg   1020
ctcccacttc ctccaaggac aattacttag agggcacttc gaccatttct gacagcgcca   1080
aggagctgtg taaggcagtg tcggtgtcca tgggcttggg tgtggaggcg ttggagcatc   1140
tgagtccagg ggaacagctt cgggggatt  gcatgtacgc cccagttttg ggagttccac   1200
ccgctgtgcg tcccactccg tgtgccccat tggccgaatg caaaggttct ctgctagacg   1260
acagcgcagg caagagcact gaagatactg ctgagtattc ccctttcaag ggaggttaca   1320
ccaaagggct agaaggcgag agcctaggct gctctggcag cgctgcagca gggagctccg   1380
ggacacttga actgccgtcc accctgtctc tctacaagtc cggagcactg gacgaggcag   1440
ctgcgtacca gagtcgcgac tactacaact ttccactggc tctggccggg ccgccgcccc   1500
ctccaccgcc tccccatccc cacgctcgca tcaagctgga gaacccgctg gactatggca   1560 gcgcctggc  ggctgcggcg gcgcagtgcc gctatgggga cctggcgagc ctgcatggcg   1620
cgggtgcagc gggaccccgg  tctgggtcac cctcagcggc cgcttcctca tcctggcaca   1680
ctctcttcac agccgaagaa ggccagttgt atggaccgtg tggtggtggg ggcggcggcg   1740
gtggcggcgg cggcggcggc gcaggcgagg cgggagctgt agccccctac ggctacactc   1800
ggccacctca ggggctggcg ggccaggaag gcgacttcac cgcacctgat gtgtggtacc   1860
ctggcggcat ggtgagcaga gtgccctatc ccagtcccac ttgtgtcaaa agcgagatgg   1920
gcccctggat ggatagctac tccggacctt acggggacat gcgtttggag actgccaggg   1980
accatgtttt gccaattgac tattactttc caccccagaa gacctgcctg atctgtggag   2040
atgaagcttc tgggtgtcac tatggagctc tcacatgtgg aagctgcaag gtcttcttca   2100
aaagagccgc tgaagggaaa cagaagtacc tgtgtgccag cagaaatgat tgcactattg   2160
ataaattccg aaggaaaaat tgtccatctt gccgtcttcg gaaatgttat gaagcaggga   2220
tgactctggg agcccggaag ctgaagaaac ttggtaatct gaaactacag gaggaaggag   2280
aggcttccag caccaccagc cccactgagg agacagccca gaagctgaca gtgtcacaca   2340
ttgaaggcta tgaatgtcag cccatctttc tgaatgtcct ggaggccatt gagccaggtg   2400
tggtgtgtgc tggacatgac aacaaccagc ccgactcctt cgcagccttg ctctctagcc   2460
tcaatgaact gggagagaga cagcttgtac atgtggtcaa gtgggccaag gccttgcctg   2520
gcttccgcaa cttacacgtg gacgaccaga tggctgtcat tcagtactcc tggatggggc   2580
tcatggtgtt tgccatgggc tggcgatcct tcaccaatgt caactccagg atgtctctact   2640 ttgcccctga tctggttttc aatgagtacc gcatgcacaa atcccggatg tacagccagt   2700
gtgtccgaat gaggcacctc tctcaagagt ttgatggct  ccaaatcacc ccccaggaat   2760
tcctgtgcat gaaagcgctg ctactcttca gcattattcc agtggatggg ctgaaaaatc   2820
```

-continued

```
aaaaattctt tgatgaactt cgaatgaact acatcaagga actcgatcgt atcattgcat    2880
gcaaaagaaa aatcccaca tcctgctcaa ggcgtttcta ccagctcacc aagctcctgg    2940
actccgtgca gcctattgcg agagagctgc atcagttcac ttttgacctg ctaatcaagt    3000
cacacatggt gagcgtggac tttccggaaa tgatggcaga gatcatctct gtgcaagtgc    3060
ccaagatcct ttctgggaaa gtcaagccca tctatttcca cacccagtga agcattggaa    3120
atccctattt cctcacccca gctcatgccc cctttcagat gtcttctgcc tgtta          3175
```

<210> SEQ ID NO 2
<211> LENGTH: 895
<212> TYPE: PRT
<213> ORGANISM: Macaca mulatta

<400> SEQUENCE: 2

```
Met Glu Val Gln Leu Gly Leu Gly Arg Val Tyr Pro Arg Pro Pro Ser
 1               5                  10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Gln Gln Gln Gln Gln Gln Gln Gln Glu Thr
    50                  55                  60

Ser Pro Arg Gln Gln Gln Gln Gln Gln Gly Glu Asp Gly Ser Pro
65                  70                  75                  80

Gln Ala His Arg Arg Gly Pro Thr Gly Tyr Leu Val Leu Asp Glu Glu
                85                  90                  95

Gln Gln Pro Ser Gln Pro Gln Ser Ala Pro Glu Cys His Pro Glu Arg
            100                 105                 110

Gly Cys Val Pro Glu Pro Gly Ala Ala Val Ala Ala Gly Lys Gly Leu
        115                 120                 125

Pro Gln Gln Leu Pro Ala Pro Pro Asp Glu Asp Asp Ser Ala Ala Pro
    130                 135                 140

Ser Thr Leu Ser Leu Leu Gly Pro Thr Phe Pro Gly Leu Ser Ser Cys
145                 150                 155                 160

Ser Ala Asp Leu Lys Asp Ile Leu Ser Glu Ala Ser Thr Met Gln Leu
                165                 170                 175

Leu Gln Gln Gln Gln Gln Glu Ala Val Ser Glu Gly Ser Ser Ser Gly
            180                 185                 190

Arg Ala Arg Glu Ala Ser Gly Ala Pro Thr Ser Ser Lys Asp Asn Tyr
        195                 200                 205

Leu Glu Gly Thr Ser Thr Ile Ser Asp Ser Ala Lys Glu Leu Cys Lys
    210                 215                 220

Ala Val Ser Val Ser Met Gly Leu Gly Val Glu Ala Leu Glu His Leu
225                 230                 235                 240

Ser Pro Gly Glu Gln Leu Arg Gly Asp Cys Met Tyr Ala Pro Val Leu
                245                 250                 255

Gly Val Pro Pro Ala Val Arg Pro Thr Pro Cys Ala Pro Leu Ala Glu
            260                 265                 270

Cys Lys Gly Ser Leu Leu Asp Asp Ser Ala Gly Lys Ser Thr Glu Asp
        275                 280                 285

Thr Ala Glu Tyr Ser Pro Phe Lys Gly Gly Tyr Thr Lys Gly Leu Glu
    290                 295                 300

Gly Glu Ser Leu Gly Cys Ser Gly Ser Ala Ala Ala Gly Ser Ser Gly
305                 310                 315                 320
```

-continued

```
Thr Leu Glu Leu Pro Ser Thr Leu Ser Leu Tyr Lys Ser Gly Ala Leu
            325                 330                 335

Asp Glu Ala Ala Ala Tyr Gln Ser Arg Asp Tyr Tyr Asn Phe Pro Leu
            340                 345                 350

Ala Leu Ala Gly Pro Pro Pro Pro Pro Pro Pro His Pro His Ala
            355                 360                 365

Arg Ile Lys Leu Glu Asn Pro Leu Asp Tyr Gly Ser Ala Trp Ala Ala
            370                 375                 380

Ala Ala Ala Gln Cys Arg Tyr Gly Asp Leu Ala Ser Leu His Gly Ala
385                 390                 395                 400

Gly Ala Ala Gly Pro Gly Ser Gly Ser Pro Ser Ala Ala Ser Ser
            405                 410                 415

Ser Trp His Thr Leu Phe Thr Ala Glu Gly Gln Leu Tyr Gly Pro
            420                 425                 430

Cys Gly Gly Gly Gly Gly Gly Gly Gly Gly Gly Gly Ala Gly
            435                 440                 445

Glu Ala Gly Ala Val Ala Pro Tyr Gly Tyr Thr Arg Pro Pro Gln Gly
            450                 455                 460

Leu Ala Gly Gln Glu Gly Asp Phe Thr Ala Pro Asp Val Trp Tyr Pro
465                 470                 475                 480

Gly Gly Met Val Ser Arg Val Pro Tyr Pro Ser Pro Thr Cys Val Lys
            485                 490                 495

Ser Glu Met Gly Pro Trp Met Asp Ser Tyr Ser Gly Pro Tyr Gly Asp
            500                 505                 510

Met Arg Leu Glu Thr Ala Arg Asp His Val Leu Pro Ile Asp Tyr Tyr
            515                 520                 525

Phe Pro Pro Gln Lys Thr Cys Leu Ile Cys Gly Asp Glu Ala Ser Gly
            530                 535                 540

Cys His Tyr Gly Ala Leu Thr Cys Gly Ser Cys Lys Val Phe Phe Lys
545                 550                 555                 560

Arg Ala Ala Glu Gly Lys Gln Lys Tyr Leu Cys Ala Ser Arg Asn Asp
            565                 570                 575

Cys Thr Ile Asp Lys Phe Arg Arg Lys Asn Cys Pro Ser Cys Arg Leu
            580                 585                 590

Arg Lys Cys Tyr Glu Ala Gly Met Thr Leu Gly Ala Arg Lys Leu Lys
            595                 600                 605

Lys Leu Gly Asn Leu Lys Leu Gln Glu Glu Gly Glu Ala Ser Ser Thr
            610                 615                 620

Thr Ser Pro Thr Glu Glu Thr Ala Gln Lys Leu Thr Val Ser His Ile
625                 630                 635                 640

Glu Gly Tyr Glu Cys Gln Pro Ile Phe Leu Asn Val Leu Glu Ala Ile
            645                 650                 655

Glu Pro Gly Val Val Cys Ala Gly His Asp Asn Asn Gln Pro Asp Ser
            660                 665                 670

Phe Ala Ala Leu Leu Ser Ser Leu Asn Glu Leu Gly Glu Arg Gln Leu
            675                 680                 685

Val His Val Val Lys Trp Ala Lys Ala Leu Pro Gly Phe Arg Asn Leu
            690                 695                 700

His Val Asp Asp Gln Met Ala Val Ile Gln Tyr Ser Trp Met Gly Leu
705                 710                 715                 720

Met Val Phe Ala Met Gly Trp Arg Ser Phe Thr Asn Val Asn Ser Arg
            725                 730                 735
```

```
Met Leu Tyr Phe Ala Pro Asp Leu Val Phe Asn Glu Tyr Arg Met His
            740                 745                 750

Lys Ser Arg Met Tyr Ser Gln Cys Val Arg Met Arg His Leu Ser Gln
        755                 760                 765

Glu Phe Gly Trp Leu Gln Ile Thr Pro Gln Glu Phe Leu Cys Met Lys
    770                 775                 780

Ala Leu Leu Leu Phe Ser Ile Ile Pro Val Asp Gly Leu Lys Asn Gln
785                 790                 795                 800

Lys Phe Phe Asp Glu Leu Arg Met Asn Tyr Ile Lys Glu Leu Asp Arg
                805                 810                 815

Ile Ile Ala Cys Lys Arg Lys Asn Pro Thr Ser Cys Ser Arg Arg Phe
                820                 825                 830

Tyr Gln Leu Thr Lys Leu Leu Asp Ser Val Gln Pro Ile Ala Arg Glu
            835                 840                 845

Leu His Gln Phe Thr Phe Asp Leu Leu Ile Lys Ser His Met Val Ser
        850                 855                 860

Val Asp Phe Pro Glu Met Met Ala Glu Ile Ile Ser Val Gln Val Pro
865                 870                 875                 880

Lys Ile Leu Ser Gly Lys Val Lys Pro Ile Tyr Phe His Thr Gln
                885                 890                 895

<210> SEQ ID NO 3
<211> LENGTH: 3175
<212> TYPE: DNA
<213> ORGANISM: Macaca mulatta

<400> SEQUENCE: 3
```

| | | | | | |
|---|---|---|---|---|---|
| cccaaaaaat | aaaacaaac | aaaaacaaaa | caaaacaaaa | aaaacgaata | aagaaaaagg | 60 |
| taataactca | gttcttattt | gcacctactt | ccagtggaca | ctgaatttgg | aaggtggagg | 120 |
| attcttgttt | tttcttttaa | gatcgggcat | cttttgaatc | tacccctcaa | gtgttaagag | 180 |
| acagactgtg | agcctagcag | ggcagatctt | gtccaccgtg | tgtcttcttt | tgcaggagac | 240 |
| tttgaggctg | tcagagcgct | ttttgcgtgg | ttgctcccgc | aagtttcctt | ctctggagct | 300 |
| tcccgcaggt | gggcagctag | ctgcagcgac | taccgcatca | tcacagcctg | ttgaactctt | 360 |
| ctgagcaaga | gaaggggagg | cggggtaagg | gaagtaggtg | gaagattcag | ccaagctcaa | 420 |
| ggatggaggt | gcagttaggg | ctggggaggt | tctaccctcg | gccgccgtcc | aagacctacc | 480 |
| gaggagcttt | ccagaatctg | ttccagagcg | tgcgcgaagt | gatccagaac | ccgggcccca | 540 |
| ggcacccaga | ggccgcgagc | gcagcacctc | ccggcgccag | tttgcagcag | cagcagcagc | 600 |
| agcagcaaga | aactagcccc | cggcaacagc | agcagcagca | gcagggtgag | gatggttctc | 660 |
| cccaagccca | tcgtagaggc | cccacaggct | acctggtcct | ggatgaggaa | cagcagcctt | 720 |
| cacagcctca | gtcagccccg | gagtgccacc | ccgagagagg | ttgcgtccca | gagcctggag | 780 |
| ccgccgtggc | cgccggcaag | gggctgccgc | agcagctgcc | agcacctccg | gacgaggatg | 840 |
| actcagctgc | cccatccacg | ttgtctctgc | tgggccccac | tttccccggc | ttaagcagct | 900 |
| gctccgccga | ccttaaagac | atcctgagcg | aggccagcac | catgcaactc | cttcagcaac | 960 |
| agcagcagga | agcagtatcc | gaaggcagca | gcagcgggag | agcgagggag | gcctcggggg | 1020 |
| ctccccactt | ctccaaggac | aattacttag | ggggcacttc | gaccatttct | gacagcgcca | 1080 |
| aggagctgtg | taaggcagtg | tcggtgtcca | tgggcttggg | tgtggaggcg | ttggagcatc | 1140 |
| tgagtccagg | ggaacagctt | cgggggatt | gcatgtacgc | cccagttttg | ggagttccac | 1200 |
| ccgctgtgcg | tcccactccg | tgtgccccat | ggccgaatg | caaaggttct | ctgctagacg | 1260 |

-continued

| | |
|---|---|
| acagcgcagg caagagcact gaagatactg ctgagtattc ccctttcaag ggaggttaca | 1320 |
| ccaaagggct agaaggcgag agcctaggct gctctggcag cgctgcagca gggagctccg | 1380 |
| ggacacttga actgccgtcc accctgtctc tctacaagtc cggagcactg gacgaggcag | 1440 |
| ctgcgtacca gagtcgcgac tactacaact ttccactggc tctggccggg ccgccgcccc | 1500 |
| ctccaccgcc tccccatccc cacgctcgca tcaagctgga gaacccgctg gactatggca | 1560 |
| gcgcctgggc ggctgcggcg gcgcagtgcc gctatgggga cctggcgagc ctgcatggcg | 1620 |
| cgggtgcagc gggacccggc tctgggtcac cctcagcggc cgcttcctca tcctggcaca | 1680 |
| ctctcttcac agccgaagaa ggccagttgt atggaccgtg tggtggtggg ggcggcggcg | 1740 |
| gtggcggcgg cggcggcggc gcaggcgagg cgggagctgt agcccctac ggctacactc | 1800 |
| ggccacctca ggggctggcg ggccaggaag gcgacttcac cgcacctgat gtgtggtacc | 1860 |
| ctggcggcat ggtgagcaga gtgccctatc ccagtccac ttgtgtcaaa gcgagatgg | 1920 |
| gcccctggat ggatagctac tccggacctt acggggacat gcgtttggag actgccaggg | 1980 |
| accatgtttt gccaattgac tattactttc cacccagaa gacctgcctg atctgtggag | 2040 |
| atgaagcttc tgggtgtcac tatggagctc tcacatgtgg aagctgcaag gtcttcttca | 2100 |
| aaagagccgc tgaagggaaa cagaagtacc tgtgtgccag cagaaatgat tgcactattg | 2160 |
| ataaattccg aaggaaaaat tgtccatctt gccgtcttcg gaaatgttat gaagcaggga | 2220 |
| tgactctggg agcccggaag ctgaagaaac ttggtaatct gaaactacag gaggaaggag | 2280 |
| aggcttccag caccaccagc cccactgagg agacagccca gaagctgaca gtgtcacaca | 2340 |
| ttgaaggcta tgaatgtcag cccatctttc tgaatgtcct ggaggccatt gagccaggtg | 2400 |
| tggtgtgtgc tggacatgac aacaaccagc ccgactcctt cgcagccttg ctctctagcc | 2460 |
| tcaatgaact gggagagaga cagcttgtac atgtggtcaa gtgggccaag gccttgcctg | 2520 |
| gcttccgcaa cttacacgtg gacgaccaga tggctgtcat tcagtactcc tggatggggc | 2580 |
| tcatggtgtt tgccatgggc tggcgatcct tcaccaatgt caactccagg atgctctact | 2640 |
| ttgcccctga tctggttttc aatgagtacc gcatgcacaa atcccggatg tacagccagt | 2700 |
| gtgtccgaat gaggcacctc tctcaagagt ttggatggct ccaaatcacc ccccaggaat | 2760 |
| tcctgtgcat gaaagcgctg ctactcttca gcattattcc agtggatggg ctgaaaaatc | 2820 |
| aaaaattctt tgatgaactt cgaatgaact acatcaagga actcgatcgt atcattgcat | 2880 |
| gcaaagaaa aaatcccaca tcctgctcaa ggcgtttcta ccagctcacc aagctcctgg | 2940 |
| actccgtgca gcctattgcg agagagctgc atcagttcac ttttgacctg ctaatcaagt | 3000 |
| cacacatggt gagcgtggac tttccggaaa tgatggcaga gatcatctct gtgcaagtgc | 3060 |
| ccaagatcct ttctgggaaa gtcaagccca tctatttcca cacccagtga agcattggaa | 3120 |
| atccctattt cctcaccccca gctcatgccc cctttcagat gtcttctgcc tgtta | 3175 |

<210> SEQ ID NO 4
<211> LENGTH: 895
<212> TYPE: PRT
<213> ORGANISM: Macaca mulatta

<400> SEQUENCE: 4

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

-continued

```
Val Ile Gln Asn Pro Gly Pro Arg His Pro Glu Ala Ala Ser Ala Ala
        35                  40                  45
Pro Pro Gly Ala Ser Leu Gln Gln Gln Gln Gln Gln Gln Gln Glu Thr
 50                  55                  60
Ser Pro Arg Gln Gln Gln Gln Gln Gln Gly Glu Asp Gly Ser Pro
 65                  70                  75                  80
Gln Ala His Arg Arg Gly Pro Thr Gly Tyr Leu Val Leu Asp Glu Glu
                 85                  90                  95
Gln Gln Pro Ser Gln Pro Gln Ser Ala Pro Glu Cys His Pro Glu Arg
                100                 105                 110
Gly Cys Val Pro Glu Pro Gly Ala Val Ala Ala Gly Lys Gly Leu
            115                 120                 125
Pro Gln Gln Leu Pro Ala Pro Pro Asp Glu Asp Ser Ala Ala Pro
    130                 135                 140
Ser Thr Leu Ser Leu Leu Gly Pro Thr Phe Pro Gly Leu Ser Ser Cys
145                 150                 155                 160
Ser Ala Asp Leu Lys Asp Ile Leu Ser Glu Ala Ser Thr Met Gln Leu
                165                 170                 175
Leu Gln Gln Gln Gln Glu Ala Val Ser Glu Gly Ser Ser Ser Gly
                180                 185                 190
Arg Ala Arg Glu Ala Ser Gly Ala Pro Thr Ser Ser Lys Asp Asn Tyr
            195                 200                 205
Leu Gly Gly Thr Ser Thr Ile Ser Asp Ser Ala Lys Glu Leu Cys Lys
    210                 215                 220
Ala Val Ser Val Ser Met Gly Leu Gly Val Glu Ala Leu Glu His Leu
225                 230                 235                 240
Ser Pro Gly Glu Gln Leu Arg Gly Asp Cys Met Tyr Ala Pro Val Leu
                245                 250                 255
Gly Val Pro Pro Ala Val Arg Pro Thr Pro Cys Ala Pro Leu Ala Glu
            260                 265                 270
Cys Lys Gly Ser Leu Leu Asp Asp Ser Ala Gly Lys Ser Thr Glu Asp
    275                 280                 285
Thr Ala Glu Tyr Ser Pro Phe Lys Gly Gly Tyr Thr Lys Gly Leu Glu
    290                 295                 300
Gly Glu Ser Leu Gly Cys Ser Gly Ser Ala Ala Ala Gly Ser Ser Gly
305                 310                 315                 320
Thr Leu Glu Leu Pro Ser Thr Leu Ser Leu Tyr Lys Ser Gly Ala Leu
                325                 330                 335
Asp Glu Ala Ala Ala Tyr Gln Ser Arg Asp Tyr Tyr Asn Phe Pro Leu
                340                 345                 350
Ala Leu Ala Gly Pro Pro Pro Pro Pro Pro Pro His Pro His Ala
            355                 360                 365
Arg Ile Lys Leu Glu Asn Pro Leu Asp Tyr Gly Ser Ala Trp Ala Ala
    370                 375                 380
Ala Ala Ala Gln Cys Arg Tyr Gly Asp Leu Ala Ser Leu His Gly Ala
385                 390                 395                 400
Gly Ala Ala Gly Pro Gly Ser Gly Ser Pro Ser Ala Ala Ser Ser
                405                 410                 415
Ser Trp His Thr Leu Phe Thr Ala Glu Glu Gly Gln Leu Tyr Gly Pro
            420                 425                 430
Cys Gly Gly Gly Gly Gly Gly Gly Gly Gly Gly Gly Ala Gly
    435                 440                 445
Glu Ala Gly Ala Val Ala Pro Tyr Gly Tyr Thr Arg Pro Pro Gln Gly
```

-continued

```
            450                 455                 460
Leu Ala Gly Gln Glu Gly Asp Phe Thr Ala Pro Asp Val Trp Tyr Pro
465                 470                 475                 480

Gly Gly Met Val Ser Arg Val Pro Tyr Pro Ser Pro Thr Cys Val Lys
                485                 490                 495

Ser Glu Met Gly Pro Trp Met Asp Ser Tyr Ser Gly Pro Tyr Gly Asp
                500                 505                 510

Met Arg Leu Glu Thr Ala Arg Asp His Val Leu Pro Ile Asp Tyr Tyr
                515                 520                 525

Phe Pro Pro Gln Lys Thr Cys Leu Ile Cys Gly Asp Glu Ala Ser Gly
                530                 535                 540

Cys His Tyr Gly Ala Leu Thr Cys Gly Ser Cys Lys Val Phe Phe Lys
545                 550                 555                 560

Arg Ala Ala Glu Gly Lys Gln Lys Tyr Leu Cys Ala Ser Arg Asn Asp
                565                 570                 575

Cys Thr Ile Asp Lys Phe Arg Arg Lys Asn Cys Pro Ser Cys Arg Leu
                580                 585                 590

Arg Lys Cys Tyr Glu Ala Gly Met Thr Leu Gly Ala Arg Lys Leu Lys
                595                 600                 605

Lys Leu Gly Asn Leu Lys Leu Gln Glu Glu Gly Glu Ala Ser Ser Thr
                610                 615                 620

Thr Ser Pro Thr Glu Glu Thr Ala Gln Lys Leu Thr Val Ser His Ile
625                 630                 635                 640

Glu Gly Tyr Glu Cys Gln Pro Ile Phe Leu Asn Val Leu Glu Ala Ile
                645                 650                 655

Glu Pro Gly Val Val Cys Ala Gly His Asp Asn Asn Gln Pro Asp Ser
                660                 665                 670

Phe Ala Ala Leu Leu Ser Ser Leu Asn Glu Leu Gly Glu Arg Gln Leu
                675                 680                 685

Val His Val Val Lys Trp Ala Lys Ala Leu Pro Gly Phe Arg Asn Leu
                690                 695                 700

His Val Asp Asp Gln Met Ala Val Ile Gln Tyr Ser Trp Met Gly Leu
705                 710                 715                 720

Met Val Phe Ala Met Gly Trp Arg Ser Phe Thr Asn Val Asn Ser Arg
                725                 730                 735

Met Leu Tyr Phe Ala Pro Asp Leu Val Phe Asn Glu Tyr Arg Met His
                740                 745                 750

Lys Ser Arg Met Tyr Ser Gln Cys Val Arg Met Arg His Leu Ser Gln
                755                 760                 765

Glu Phe Gly Trp Leu Gln Ile Thr Pro Gln Glu Phe Leu Cys Met Lys
                770                 775                 780

Ala Leu Leu Leu Phe Ser Ile Ile Pro Val Asp Gly Leu Lys Asn Gln
785                 790                 795                 800

Lys Phe Phe Asp Glu Leu Arg Met Asn Tyr Ile Lys Glu Leu Asp Arg
                805                 810                 815

Ile Ile Ala Cys Lys Arg Lys Asn Pro Thr Ser Cys Ser Arg Arg Phe
                820                 825                 830

Tyr Gln Leu Thr Lys Leu Leu Asp Ser Val Gln Pro Ile Ala Arg Glu
                835                 840                 845

Leu His Gln Phe Thr Phe Asp Leu Leu Ile Lys Ser His Met Val Ser
                850                 855                 860

Val Asp Phe Pro Glu Met Met Ala Glu Ile Ile Ser Val Gln Val Pro
865                 870                 875                 880
```

Lys Ile Leu Ser Gly Lys Val Lys Pro Ile Tyr Phe His Thr Gln
            885                 890                 895

<210> SEQ ID NO 5
<211> LENGTH: 3175
<212> TYPE: DNA
<213> ORGANISM: Macaca mulatta

<400> SEQUENCE: 5

| | | | | | |
|---|---|---|---|---|---|
| gggtttttta | tttttgtttg | tttttgtttt | gttttgtttt | ttttgcttat | ttcttttttcc | 60 |
| attattgagt | caagaataaa | cgtggatgaa | ggtcacctgt | gacttaaacc | ttccacctcc | 120 |
| taagaacaaa | aaagaaaatt | ctagcccgta | gaaaacttag | atggggagtt | cacaattctc | 180 |
| tgtctgacac | tcggatcgtc | ccgtctagaa | caggtggcac | acagaagaaa | acgtcctctg | 240 |
| aaactccgac | agtctcgcga | aaaacgcacc | aacgagggcg | ttcaaaggaa | gagacctcga | 300 |
| agggcgtcca | cccgtcgatc | gacgtcgctg | atggcgtagt | agtgtcggac | aacttgagaa | 360 |
| gactcgttct | cttcccctcc | gccccattcc | cttcatccac | cttctaagtc | ggttcgagtt | 420 |
| cctacctcca | cgtcaatccc | gacccctccc | agatgggagc | cggcggcagg | ttctggatgg | 480 |
| ctcctcgaaa | ggtcttagac | aaggtctcgc | acgcgcttca | ctaggtcttg | ggcccggggt | 540 |
| ccgtgggtct | ccggcgctcg | cgtcgtggag | ggccgcggtc | aaacgtcgtc | gtcgtcgtcg | 600 |
| tcgtcgttct | ttgatcgggg | gccgttgtcg | tcgtcgtcgt | cgtcccactc | ctaccaagag | 660 |
| gggtcgggt | agcatctccg | gggtgtccga | tggaccagga | cctactcctt | gtcgtcggaa | 720 |
| gtgtcggagt | cagtcggggc | ctcacggtgg | ggctctctcc | aacgcagggt | ctcggacctc | 780 |
| ggcggcaccg | gcggccgttc | cccgacggcg | tcgtcgacgg | tcgtggaggc | ctgctcctac | 840 |
| tgagtcgacg | gggtaggtgc | aacagagacg | acccggggtg | aaaggggccg | aattcgtcga | 900 |
| cgaggcggct | ggaatttctg | taggactcgc | tccggtcgtg | gtacgttgag | gaagtcgttg | 960 |
| tcgtcgtcct | tcgtcatagg | cttccgtcgt | cgtcgccctc | tcgctccctc | cggagccccc | 1020 |
| gagggtgaag | gaggttcctg | ttaatgaatc | tcccgtgaag | ctggtaaaga | ctgtcgcggt | 1080 |
| tcctcgacac | attccgtcac | agccacaggt | acccgaaccc | acacctccgc | aacctcgtag | 1140 |
| actcaggtcc | ccttgtcgaa | gcccccctaa | cgtacatgcg | gggtcaaaac | cctcaaggtg | 1200 |
| ggcgacacgc | agggtgaggc | acacggggta | accggcttac | gtttccaaga | gacgatctgc | 1260 |
| tgtcgcgtcc | gttctcgtga | cttctatgac | gactcataag | gggaaagttc | cctccaatgt | 1320 |
| ggtttcccga | tcttccgctc | tcggatccga | cgagaccgtc | gcgacgtcgt | ccctcgaggc | 1380 |
| cctgtgaact | tgacggcagg | tgggacagag | agatgttcag | gcctcgtgac | ctgctccgtc | 1440 |
| gacgcatggt | ctcagcgctg | atgatgttga | aaggtgaccg | agaccggccc | ggcggcgggg | 1500 |
| gaggtggcgg | aggggtaggg | gtgcgagcgt | agttcgacct | cttgggcgac | ctgataccgt | 1560 |
| cgcggacccg | ccgacgccgc | cgcgtcacgg | cgataccct | ggaccgctcg | acgtaccgc | 1620 |
| gcccacgtcg | ccctgggccg | agaccagtg | ggagtcgccg | gcgaaggagt | aggaccgtgt | 1680 |
| gagagaagtg | tcggcttctt | ccggtcaaca | tacctggcac | accaccaccc | ccgccgccgc | 1740 |
| caccgccgcc | gccgccgccg | cgtccgctcc | gccctcgaca | tcggggatg | ccgatgtgag | 1800 |
| ccggtggagt | ccccgaccgc | ccggtccttc | cgctgaagtg | gcgtggacta | cacaccatgg | 1860 |
| gaccgccgta | ccactcgtct | cacgggatag | ggtcagggtg | aacacagttt | tcgctctacc | 1920 |
| cggggaccta | cctatcgatg | aggcctggaa | tgccctgta | cgcaaacctc | tgacggtccc | 1980 |
| tggtacaaaa | cggttaactg | ataatgaaag | gtggggtctt | ctggacggac | tagacacctc | 2040 |

```
tacttcgaag acccacagtg atacctcgag agtgtacacc ttcgacgttc cagaagaagt   2100
tttctcggcg acttcccttt gtcttcatgg acacacggtc gtctttacta acgtgataac   2160
tatttaaggc ttcctttta acaggtagaa cggcagaagc ctttacaata cttcgtccct    2220
actgagaccc tcgggccttc gacttctttg aaccattaga ctttgatgtc ctccttcctc   2280
tccgaaggtc gtggtggtcg ggtgactcc tctgtcgggt cttcgactgt cacagtgtgt    2340
aacttccgat acttacagtc gggtagaaag acttacagga cctccggtaa ctcggtccac   2400
accacacacg acctgtactg ttgttggtcg ggctgaggaa cgtcggaac gagagatcgg    2460
agttacttga ccctctctct gtcgaacatg tacaccagtt cacccggttc cggaacggac   2520
cgaaggcgtt gaatgtgcac ctgctggtct accgacagta agtcatgagg acctaccccg   2580
agtaccacaa acggtacccg accgctagga agtggttaca gttgaggtcc tacgagatga   2640
aacgggggact agaccaaaag ttactcatgg cgtacgtgtt tagggcctac atgtcggtca   2700
cacaggctta ctccgtggag agagttctca aacctaccga ggtttagtgg gggtcctta    2760
aggacacgta ctttcgcgac gatgagaagt cgtaataagg tcacctaccc gactttttag   2820
tttttaagaa actacttgaa gcttacttga tgtagttcct tgagctagca tagtaacgta   2880
cgttttcttt tttagggtgt aggacgagtt ccgcaaagat ggtcgagtgg ttcgaggacc   2940
tgaggcacgt cggataacgc tctctcgacg tagtcaagtg aaaactggac gattagttca   3000
gtgtgtacca ctcgcacctg aaaggccttt actaccgtct ctagtagaga cacgttcacg   3060
ggttctagga aagacccttt cagttcgggt agataaaggt gtgggtcact tcgtaacctt   3120
tagggataaa ggagtgtggg cgagtacggg ggaaagtcta cagaagacgg acaat        3175
```

<210> SEQ ID NO 6
<211> LENGTH: 2821
<212> TYPE: DNA
<213> ORGANISM: Macaca fascicularis
<400> SEQUENCE: 6

```
atggaggtgc agttagggct ggggagggtc taccctcggc cgccgtccaa gacctaccga    60
ggagctttcc agaatctgtt ccagagcgtg cgcgaagtga tccagaaccc gggccccagg   120
cacccagagg ccgcgagcgc agcacctccc ggcgccagtt tgcagcagca gcagcagcag   180
cagcaagaaa ctagcccccg gcaacagcag cagcagcagc agggtgagga tggttctccc   240
caagcccatc gtagaggccc cacaggctac ctggtcctgg atgaggaaca gcagccttca   300
cagcctcagt cagccccgga gtgccacccc gagagaggtt gcgtcccaga gcctggagcc   360
gccgtggccg ccggcaaggg gctgccgcag cagctgccag cacctccgga cgaggatgac   420
tcagctgccc catccacgtt gtctctgctg gccccacctt tccccggctt aagcagctgc   480
tccaccgacc ttaaagacat cctgagcgag gccagcacca tgcaactcct tcagcaacag   540
cagcaggaag cagtatccga aggcagcagc agcgggagag ccagggaggc ctcgggggct   600
cccacttcct ccaaggacaa ttacttaggg ggcacttcga ccatttctga cagcgccaag   660
gagctgtgta aggcagtgtc ggtgtccatg ggcttgggtg tggaggcgtt ggagcatctg   720
agtccagggg aacagcttcg gggggattgc atgtacgccc cagttttggg agttccaccc   780
gctgtgcgtc ccactccgtg tgccccattg gccgaatgca aggttctctc ctagacgac   840
agcgcaggca agagcactga agatactgct gagtattccc cttcaaggg aggttacacc   900
aaagggctag aaggcgagag cctaggctgc tctggcagcg ctgcagcagg gagctccggg   960
```

```
acacttgaac tgccgtccac cctgtctctc tacaagtccg gagcactgga cgaggcagct   1020
gcgtaccaga gtcgcgacta ctacaacttt ccactggctc tggccgggcc gccgccccct   1080
ccaccgcctc cccatcccca cgctcgcatc aagctggaga accgctgga ctatggcagc    1140 gcctgggcgg ctgcggcggc gcagtgccgc tatgggacc tggcgagcct gcatggcgcg    1200
ggtgcagcgg gacccggctc tgggtcaccc tcagcggccg cttcctcatc ctggcacact   1260
ctcttcacag ccgaagaagg ccagttgtat ggaccgtgtg gtggtggggg cggcggcggt   1320
ggcggcggcg gcggcggcgc aggcgaggcg ggagctgtag cccctacgg ctacactcgg    1380 ccacctcagg ggctggcggg ccaggaaggc gacttcaccg cacctgatgt gtggtaccct   1440
ggcggcatgg tgagcagagt gccctatccc agtcccactt gtgtcaaaag cgagatgggc   1500
ccctggatga tagctactc cggaccttac ggggacatgc ggttggagac tgccagggac    1560
catgttttgc caattgacta ttactttcca ccccagaaga cctgcctgat ctgtggagat   1620
gaagcttctg ggtgtcacta tggagctctc acatgtggaa gctgcaaggt cttcttcaaa   1680
agagccgctg aagggaaaca gaagtacctg tgtgccagca gaaatgattg cactattgat   1740
aaattccgaa ggaaaaattg tccatcttgc cgtcttcgga atgttatga agcagggatg     1800 actctgggag cccggaagct gaagaaactt ggtaatctga actacagga ggaaggagag    1860 gcttccagca ccaccagccc cactgaggag acagcccaga agctgacagt gtcacacatt   1920
gaaggctatg aatgtcagcc catctttctg aatgtcctgg aagccattga ccaggtgtg    1980 gtgtgtgctg acatgacaa caaccagccc gactccttcg cagccttgct ctctagcctc    2040
aatgaactgg gagagagaca gcttgtacat gtggtcaagt gggccaaggc cttgcctggc   2100
ttccgcaact tacacgtgga cgaccagatg gctgtcattc agtactcctg gatggggctc    2160
atggtgtttg ccatgggctg gcgatccttc accaatgtca actccaggat gctctacttt   2220
gcccctgatc tggttttcaa tgagtaccgc atgcacaagt cccggatgta cagccagtgt   2280
gtccgaatga ggcacctctc tcaagagttt ggatggctcc aaatcacccc caggaattc    2340 ctgtgcatga aagcgctgct actcttcagc attattccag tggatgggct gaaaaatcaa   2400
aaattctttg atgaacttcg aatgaactac atcaaggaac tcgatcgtat cattgcatgc   2460
aaaagaaaaa atcccacatc ctgctcaagg cgtttctacc agctcaccaa gctcctggac   2520
tccgtgcagc ctattgcgag agagctgcat cagttcactt ttgacctgct aatcaagtca   2580
cacatggtga gcgtggactt tccggaaatg atggcagaga tcatctctgt gcaagtgccc   2640
aaaatccttt ctgggaaagt caagcccatc tatttccaca cccagtgaag cattggaaat   2700
ccctatttcc tcaccccagc tcatgccccc tttcagatgt cttctgcctg ttataactct   2760
gcactactcc tctgcagtgc cttggggaat ttcctctatt gatgtacagt ctgtcatgaa   2820
c                                                                   2821
```

<210> SEQ ID NO 7
<211> LENGTH: 329
<212> TYPE: DNA
<213> ORGANISM: Macaca mulatta

<400> SEQUENCE: 7

```
tctcaagagt ttggatggct ccaaatcacc ccccaggaat tcctgtgcat gaaagcgctg    60
ctactcttca gcattattcc agtggatggg ctgaaaaatc aaaaattctt tgatgaactt   120
cgaatgaact acatcaagga actcgatcgt atcattgcat gcaaaagaaa aaatcccaca   180
tcctgctcaa ggcgtttcta ccagctcacc aagctcctgg actccgtgca gcctattgcg   240
```

```
agagagctgc atcagttcac ttttgacctg ctaatcaagt cacacatggt gagcgtggac      300
tttccggaaa tgatggcaga gatcatctc                                        329

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
atggaggtgc agttagggct g                                                21

<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9
ggtcttctgg ggtggaaagt a                                                21

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
acggctacac tcggccacct c                                                21

<210> SEQ ID NO 11
<211> LENGTH: 21
<212> TYPE: DNA
<213> ORGANISM: Artificial Sequence
<220> FEATURE:
<223> OTHER INFORMATION: PCR primer

<400> SEQUENCE: 11
aacaggcaga agacatctga a                                                21

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
ggcggccgag ggtagaccct c                                                21
```

What is claimed:

1. A purified DNA molecule encoding a *Macaca mulatta* AR protein wherein said protein comprises the amino acid sequence as follows:

```
MEVQLGLGRV  YPRPPSKTYR  GAFQNLFQSV  REVIQNPGPR
HPEAASAAPP  GASLQQQQQQ  QQETSPRQQQ  QQQQGEDGSP
QAHRRGPTGY  LVLDEEQQPS  QPQSAPECHP  ERGCVPEPGA
AVAAGKGLPQ  QLPAPPDEDD  SAAPSTLSLL  GPTFPGLSSC
SADLKDILSE  ASTMQLLQQQ  QQEAVSEGSS  SGRAREASGA
PTSSKDNYLE  GTSTISDSAK  ELCKAVSVSM  GLGVEALEHL
SPGEQLRGDC  MYAPVLGVPP  AVRPTPCAPL  AECKGSLLDD
SAGKSTEDTA  EYSPFKGGYT  KGLEGESLGC  SGSAAAGSSG
TLELPSTLSL  YKSGALDEAA  AYQSRDYYNF  PLALAGPPPP
PPPPHPHARI  KLENPLDYGS  AWAAAAAQCR  YGDLASLHGA
GAAGPGSGSP  SAAASSSWHT  LFTABEGQLY  GPCGGGGGGG
GGGGGGAGEA  GAVAPYGYTR  PPQGLAGQEG  DFTAPDVWYP
GGMVSRVPYP  SPTCVKSEMG  PWMDSYSGPY  GDMRLETAHD
HVLPIDYYFP  PQKTCLICGD  EASGCHYGAL  TCGSCKVFFK
RAAEGKQKYL  CASRNDCTID  KFRRKIWPSC  RLRKCYEAGM
TLGARKLKKL  GNLKLQEEGE  ASSTTSPTEE  TAQKLTVSHI
EGYECQPIFL  NVLEAIEPGV  VCAGHDNNQP  DSFAALLSSL
NELGERQLVH  VVKWAKALPG  FRNLHVDDQM  AVIQYSWNGL
MVFAMGWRSF  TNVNSRMLYF  APDLVFNEYR  MHKSRMYSQC
VPMRHLSQEF  GWLQITPQEF  LCMKALLLFS  IIPVDGLKNQ
KFFDELRMNY  IKELDRIIAC  KRKNPTSCSR  RFYQLTKLLD
SVQPIARELH  QFTFDLLIKS  HMVSVDFPEM  MARIISVQVP
KILSGKVKPI  YFHTQ,
``` as set forth in three-letter abbreviation in SEQ ID NO:2.

2. A DNA expression vector for expressing a *Macaca mulatta* AR protein in a recombinant host cell wherein said expression vector comprises a DNA molecule of claim 1.

3. A host cell which expresses a recombinant *Macaca mulatta* AR protein wherein said host cell contains the DNA expression vector of claim 2.

4. A process for expressing a *Macaca mulatta* AR protein in a recombinant host cell, comprising:
   (a) transfecting the expression vector of claim 2 into a suitable host cell; and
   (b) culturing the host cells of step (a) under conditions which allow expression of said the *Macaca mulatta* AR protein from said DNA expression vector.

5. A purified DNA molecule encoding a *Macaca mulatta* AR protein wherein said protein consists of the amino acid sequence as follows:

```
MEVQLGLGRV  YPRPPSKTYR  GAFQNLFQSV  REVIQNPGPR  HPEAASAAPP
GASLQQQQQQ  QQETSPRQQQ  QQQQGEDGSP  QAHRRGPTGY  LVLDEEQQPS
QPQSAPECHP  ERGCVPEPGA  AVAAGKGLPQ  QLPAPPDEDD  SAAPSTLSLL
GPTFPGLSSC  SADLKDILSE  ASTMQLLQQQ  QQEAVSEGSS  SGRAREASGA
PTSSRDNYLE  GTSTISDSAK  ELCKAVSVSM  GLGVEALEHL  SPGEQLRGDC
MYAPVLGVPP  AVRPTPCAPL  AECKGSLLDD  SAGKSTEDTA  EYSPFKGGYT
KGLEGESLGC  SGSAAAGSSG  TLELPSTLSL  YKSGALDEAA  AYQSRDYYNF
PLALAGPPPP  PPPPHPHARI  KLENPLDYGS  AWAAAAAQCR  YGDLASLHGA
GAAGPGSGSP  SAAASSSWHT  LFTAEEGQLY  GPCGGGGGGG  GGGGGGAGEA
GAVAPYGYTR  PPQGLAGQEG  DFTAPDVWYP  GGMVSRVPYP  SPTCVKSEMG
PWMDSYSGPY  GDMRLETAPD  HVLPIDYYFP  PQKTCLICGD  EASGCHYGAL
TCGSCKVFFK  RAAEGKQKYL  CASRNDCTID  KFRRKNCPSC  RLRKCYEAGM
TLGARKLKKL  GNLKLQEEGE  ASSTTSPTEE  TAQKLTVSHI  EGYECQPIFL
NVLEAIEPGV  VCAGHDNNQP  DSFAALLSSL  NELGERQLVH  VVKWAKALPG
FRNLHVDDQM  AVIQYSWMGL  MVFAMGWRSF  TNVNSRMLYF  APDLVFNEYR
MHKSRMYSQC  VRMRHLSQEF  GWLQITPQEF  LCMKALLLFS  IIPVDGLKNQ
KFFDELRMNY  IKELDRIIAC  KRKNPTSCSR  RFYQLTKLLD  SVQPIARELH
QFTFDLLIKS  HMVSVDFPEM  MAEIISVQVP  KILSGKVKPI  YFHTQ,
``` as set forth in three-letter abbreviation in SEQ ID NO:2.

6. A DNA expression vector for expressing a *Macaca mulatta* AR protein in a recombinant host cell wherein said expression vector comprises a DNA molecule of claim 5.

7. A host cell which expresses a recombinant *Macaca mulatta* AR protein wherein said host cell contains the expression vector of claim 6.

8. A process for expressing a *Macaca mulatta* AR protein in a recombinant host cell, comprising:

(a) transfecting the expression vector of claim 6 into a suitable host cell; and
(b) culturing the host cells of step (a) under conditions which allow expression of said the *Macaca mulatta* AR protein from said expression vector.

9. A purified DNA molecule encoding a *Macaca mulatta* AR protein wherein said DNA molecule comprises the nucleotide sequence, as follows:

```
CCCAAAAAAT   AAAAACAAAC   AAAAACAAAA   CAAAACAAAA   AAAACGAATA
AAGAAAAAGG   TAATAACTCA   GTTCTTATTT   GCACCTACTT   CCAGTGGACA
CTGAATTTGG   AAGGTGGAGG   ATTCTTGTTT   TTTCTTTTAA   GATCGGGCAT
CTTTTGAATC   TACCCCTCAA   GTGTTAAGAG   ACAGACTGTG   AGCCTAGCAG
GGCAGATCTT   GTCCACCGTG   TCTCTTCTTT   TGCAGGAGAC   TTTGAGGCTG
TCAGAGCGCT   TTTTGCGTGG   TTGCTCCCGC   AAGTTTCCTT   CTCTGGAGCT
TCCCGCAGGT   GGGCAGCTAG   CTGCAGCGAC   TACCGCATCA   TCACAGCCTG
TTGAACTCTT   CTGAGCAAGA   GAAGGGGAGG   CGGGGTAAGG   GAAGTAGGTG
GAAGATTCAG   CCAAGCTCAA   GGATGGACGT   GCAGTTAGGG   CTGGGGAGGG
TCTACCCTCG   GCCGCCGTCC   AAGACCTACC   GAGGAGCTTT   CCAGAATCTG
TTCCAGAGCG   TGCGCGAAGT   GATCCAGAAC   CCGGGCCCCA   GGCACCCAGA
GGCCGCGAGC   GCAGCACCTC   CCGGCGCCAG   TTTGCAGCAG   CAGCAGCAGC
AGCAGCAAGA   AACTAGCCCC   CGGCAACAGC   AGCAGCAGCA   GCAGGGTGAG
GATGGTTCTC   CCCAAGCCCA   TCGTAGAGGC   CCCACAGGCT   ACCTGGTCCT
GGATGAGGAA   CAGCAGCCTT   CACAGCCTCA   GTCAGCCCCG   GAGTGCCACC
CCGAGAGAGG   TTGCGTCCCA   GAGCCTGGAG   CCGCCGTGGC   CGCCGGCAAG
GGGCTGCCGC   AGCAGCTGCC   AGCACCTCCG   GACGAGGATG   ACTCAGCTGC
CCCATCCACG   TTGTCTCTGC   TGGGCCCCAC   TTTCCCCGGC   TTAAGCAGCT
GCTCCGCCGA   CCTTAAAGAC   ATCCTGAGCG   AGGCCAGCAC   CATGCAACTC
CTTCAGCAAC   AGCAGCAGGA   AGCAGTATCC   GAAGGCAGCA   GCAGCGGGAG
AGCGAGGGAG   GCCTCGGGGG   CTCCCACTTC   CTCCAAGGAC   AATTACTTAG
AGGGCACTTC   GACCATTTCT   GACAGCGCCA   AGCAGCTGTG   TAAGGCAGTG
TCGGTGTCCA   TGGGCTTGGG   TGTGGAGGCG   TTGGAGCATC   TGAGTCCAGG
GGAACAGCTT   CGGGGGGATT   GCATGTACGC   CCCAGTTTTG   GGAGTTCCAC
CCGCTGTGCG   TCCCACTCCG   TGTGCCCCAT   TGGCCGAATG   CAAAGGTTCT
CTGCTAGACG   ACAGCGCAGG   CAAGAGCACT   GAAGATACTG   CTGAGTATTC
CCCTTTCAAG   GGAGGTTACA   CCAAAGGGCT   AGAAGGCGAG   AGCCTAGGCT
GCTCTGGCAG   CGCTGCAGCA   GGGAGCTCCG   GGACACTTGA   ACTGCCGTCC
ACCCTGTCTC   TCTACAAGTC   CGGAGCACTG   GACGAGGCAG   CTGCGTACCA
GAGTCGCGAC   TACTACAACT   TTCCACTGGC   TCTGGCCGGG   CCGCCGCCCC
CTCCACCGCC   TCCCCATCCC   CACGCTCGCA   TCAAGCTGGA   GAACCCGCTG
GACTATGGCA   GCGCCTGGGC   GGCTGCGGCG   GCGCAGTGCC   GCTATGGGGA
CCTGGCGAGC   CTGCATGGCG   CGGGTGCAGC   GGGACCCGGC   TCTGGGTCAC
CCTCAGCGGC   CGCTTCCTCA   TCCTGGCACA   CTCTCTTCAC   AGCCGAAGAA
GGCCAGTTGT   ATGGACCGTG   TGGTGGTGGG   GGCGGCGGCG   GTGGCGGCGG
```

-continued

```
CGGCGGCGGC  GCAGGCGAGG  CGGGAGCTGT  AGCCCCCTAC  GGCTACACTC

GGCCACCTCA  GGGGCTGGCG  GGCCAGGAAG  GCGACTTCAC  CGCACCTGAT

GTGTGGTACC  CTGGCGGCAT  GGTGAGCAGA  GTGCCCTATC  CCAGTCCCAC

TTGTGTCAAA  AGCGAGATGG  GCCCCTGGAT  GGATAGCTAC  TCCGGACCTT

ACGGGGACAT  GCGTTTGGAG  ACTGCCAGGG  ACCATGTTTT  GCCAATTGAC

TATTACTTTC  CACCCCAGAA  GACCTGCCTG  ATCTGTGGAG  ATGAAGCTTC

TGGGTGTCAC  TATGGAGCTC  TCACATGTGG  AAGCTGCAAG  GTCTTCTTCA

AAAGAGCCGC  TGAAGGGAAA  CAGAAGTACC  TGTGTGCCAG  CAGAAATGAT

TGCACTATTG  ATAAATTCCG  AAGGAAAAAT  TGTCCATCTT  GCCGTCTTCG

GAAATGTTAT  GAAGCAGGGA  TGACTCTGGG  AGCCCGGAAG  CTGAAGAAAC

TTGGTAATCT  GAAACTACAG  GAGGAAGGAG  AGGCTTCCAG  CACCACCAGC

CCCACTGAGG  AGACAGGCCA  GAAGCTGACA  GTGTCACACA  TTGAAGGCTA

TGAATGTCAG  CCCATCTTTC  TGAATGTCCT  GGAGGCCATT  GAGCCAGGTG

TGGTGTGTGC  TGGACATGAC  AACAACCAGC  CCGACTCCTT  CGCAGCCTTG

CTCTCTAGCC  TCAATGAACT  GGGAGAGAGA  CAGCTTGTAC  ATGTGGTCAA

GTGGGCCAAG  GCCTTGCCTG  GCTTCCGCAA  CTTACACGTG  GACGACCAGA

TGGCTGTCAT  TCAGTACTCC  TGGATGGGGC  TCATGGTGTT  TGCCATGGGC

TGGCGATCCT  TCACCAATGT  CAACTCCAGG  ATGCTCTACT  TTGCCCCTGA

TCTGGTTTTC  AATGAGTACC  GCATGCACAA  ATCCCGGATG  TACAGCCAGT

GTGTCCGAAT  GAGGCACCTC  TCTCAAGAGT  TTGGATGGCT  CCAAATCACC

CCCCAGGAAT  TCCTGTGCAT  GAAAGCGCTG  CTACTCTTCA  GCATTATTCC

AGTGGATGGG  CTGAAAAATC  AAAAATTCTT  TGATGAACTT  CGAATGAACT

ACATCAAGGA  ACTCGATCGT  ATCATTGCAT  GCAAAAGAAA  AAATCCCACA

TCCTGCTCAA  GGCGTTTCTA  CCAGCTCACC  AAGCTCCTGG  ACTCCGTGCA

GCCTATTGCG  AGAGAGCTGC  ATCAGTTCAC  TTTTGACCTG  CTAATCAAGT

CACACATGGT  GAGCGTGGAC  TTTCCGGAAA  TGATGGCAGA  GATCATCTCT

GTGCAAGTGC  CCAAGATCCT  TTCTGGGAAA  GTCAAGCCCA  TCTATTTCCA

CACCCAGTGA  AGCATTGGAA  ATCCCTATTT  CCTCACCCCA  GCTCATGCCC

CCTTTCAGAT  GTCTTCTGCC  TGTTA,
``` set forth as SEQ ID NO:1.

10. A DNA molecule of claim 9 which consists of nucleotide 154 to about nucleotide 1257 of SEQ ID NO: 1.

11. An expression vector for expressing a *Macaca mulatta* AR protein wherein said expression vector comprises a DNA molecule of claim 9.

12. An expression vector for expressing a *Macaca mulatta* AR protein wherein said expression vector comprises a DNA molecule of claim 10.

13. A host cell which expresses a recombinant *Macaca mulatta* AR protein wherein said host cell contains the expression vector of claim 11.

14. A host cell which expresses a recombinant *Macaca mulatta* AR protein wherein said host cell contains the expression vector of claim 12.

15. A process for expressing a *Macaca mulatta* AR protein in a recombinant host cell, comprising:
(a) transfecting the expression vector of claim 11 into a suitable host cell; and,
(b) culturing the host cells of step (a) under conditions which allow expression of said the *Macaca mulatta* AR protein from said expression vector.

16. The process of claim 15 wherein the host cell is a yeast host cell.

17. A purified DNA molecule encoding a *Macaca mulatta* AR protein wherein said DNA molecule consists of the nucleotide sequence, as follows,

```
CCCAAAAAAT  AAAAACAAAC  AAAAACAAAA  CAAAACAAAA  AAAACGAATA
AAGAAAAAGG  TAATAACTCA  GTTCTTATTT  GCACCTACTT  CCAGTGGACA
CTGAATTTGG  AAGGTGGAGG  ATTCTTGTTT  TTTCTTTTAA  GATCGGGCAT
CTTTTGAATC  TACCCCTCAA  GTGTTAAGAG  ACAGACTGTG  AGCCTAGCAG
GGCAGATCTT  GTCCACCGTG  TGTCTTCTTT  TGCAGGAGAC  TTTGAGGCTG
TCAGAGCGCT  TTTTGCGTGG  TTGCTCCCGC  AAGTTTCCTT  CTCTGGAGCT
TCCCGCAGGT  GGGCAGCTAG  CTGCAGCGAC  TACCGCATCA  TCACAGCCTG
TTGAACTCTT  CTGAGCAAGA  GAAGGGGAGG  CGGGGTAAGG  GAAGTAGGTG
GAAGATTCAG  CCAAGCTCAA  GGATGGAGGT  GCAGTTAGGG  CTGGGGAGGG
TCTACCCTCG  GCCGCCGTCC  AAGACCTACC  GACGAGCTTT  CCAGAATCTG
TTCCAGAGCG  TGCGCGAAGT  GATCCAGAAC  CCGGGCCCCA  GGCACCCAGA
GGCCGCGAGC  GCAGCACCTC  CCGGCGCCAG  TTTGCAGCAG  CAGCAGCAGC
AGCAGCAAGA  AACTAGCCCC  CGGCAACAGC  AGCAGCAGCA  GCAGGGTGAG
GATGGTTCTC  CCCAAGCCCA  TCGTAGAGGC  CCCACAGGCT  ACCTGGTCCT
GGATGAGGAA  CAGCAGCCTT  CACAGCCTCA  GTCAGCCCCG  GAGTGCCACC
CCGAGAGAGG  TTGCGTCCCA  GAGCCTGGAG  CCGCCGTGGC  CGCCGGCAAG
GGGCTGCCGC  AGCAGCTGCC  AGCACCTCCG  GACGAGGATG  ACTCAGCTGC
CCCATCCACG  TTGTCTCTGC  TGGGCCCCAC  TTTCCCCGGC  TTAAGCAGCT
GCTCCGCCGA  CCTTAAAGAC  ATCCTGAGCG  AGGCCAGCAC  CATGCAACTC
CTTCAGCAAC  AGCAGCAGGA  AGCAGTATCC  GAAGGCAGCA  GCAGCGGGAG
AGCGAGGGAG  GCCTCGGGGG  CTCCCACTTC  CTCCAAGGAC  AATTACTTAG
AGGGCACTTC  GACCATTTCT  GACAGCGCCA  AGGAGCTGTG  TAAGGCAGTG
TCGGTGTCCA  TGGGCTTGGG  TGTGGAGGCG  TTGGAGCATC  TGAGTCCAGG
GGAACAGCTT  CGGGGGGATT  GCATGTACGC  CCCAGTTTTG  GGAGTTCCAC
CCGCTGTGCG  TCCCACTCCG  TGTGCCCCAT  TGGCCGAATG  CAAAGGTTCT
CTGCTAGACG  ACAGCGCAGG  CAAGAGCACT  GAAGATACTG  CTGAGTATTC
CCCTTTCAAG  GGAGGTTACA  CCAAAGGGCT  AGAAGGCGAG  AGCCTAGGCT
GCTCTGGCAG  CGCTGCAGCA  GGGAGCTCCG  GGACACTTGA  ACTGCCGTCC
ACCCTGTCTC  TCTACAAGTC  CGGAGCACTG  GACGAGGCAG  CTGCGTACCA
GAGTCGCGAC  TACTACAACT  TTCCACTGGC  TCTGGCCGGG  CCGCCGCCCC
CTCCACCGCC  TCCCCATCCC  CACGCTCGCC  TCAAGCTGGA  GAACCCGCTG
GACTATGGCA  GCGCCTGGGC  GGCTGCGGCG  GCGCAGTGCC  GCTATGGGGA
CCTGGCGAGC  CTGCATGGCG  CGGGTGCAGC  GGGACCCGGC  TCTGGGTCAC
CCTCAGCGGC  CGCTTCCTCA  TCCTGGCACA  CTCTCTTCAC  AGCCGAAGAA
GGCCAGTTGT  ATGGACCGTG  TGGTGGTGGG  GGCGGCGGCG  GTGGCGGCGG
CGGCGGCGGC  GCAGGCGAGG  CGGGAGCTGT  AGCCCCCTAC  GGCTACACTC
GGCCACCTCA  GGGGCTGGCG  GGCCAGGAAG  GCGACTTCAC  CGCACCTGAT
GTGTGGTACC  CTGGCGGCAT  GGTGAGCAGA  GTGCCCTATC  CCAGTCCCAC
TTGTGTCAAA  AGCGAGATGG  GCCCCTGGAT  GGATAGCTAC  TCCGGACCTT
ACGGGGACAT  GCGTTTGGAG  ACTGCCAGGG  ACCATGTTTT  GCCAATTGAC
```

-continued

```
TATTACTTTC   CACCCCAGAA   GACCTGCCTG   ATCTGTGGAG   ATGAAGCTTC

TGGGTGTCAC   TATGGAGCTC   TCACATGTGG   AAGCTGCAAG   GTCTTCTTCA

AAAGAGCCGC   TGAAGGGAAA   CAGAAGTACC   TGTGTGCCAG   CAGAAATGAT

TGCACTATTG   ATAAATTCCG   AAGGAAAAAT   TGTCCATCTT   GCCGTCTTCG

GAAATGTTAT   GAAGCAGGGA   TGACTCTGGG   AGCCCGGAAG   CTGAAGAAAC

TTGGTAATCT   GAAACTACAG   GAGGAAGGAG   AGGCTTCCAG   CACCACCAGC

CCCACTGAGG   AGACAGCCCA   GAAGCTGACA   GTGTCACACA   TTGAAGGCTA

TGAATGTCAG   CCCATCTTTC   TGAATGTCCT   GGAGGCCATT   GAGCCAGGTG

TGGTGTGTGC   TGGACATGAC   AACAACCAGC   CCGACTCCTT   CGCAGCCTTG

CTCTCTAGCC   TCAATGAACT   GGGAGAGAGA   CAGCTTGTAC   ATGTGGTCAA

GTGGGCCAAG   GCCTTGCCTG   GCTTCCGCAA   CTTACACGTG   GACGACCAGA

TGGCTGTCAT   TCAGTACTCC   TGGATGGGGC   TCATGGTGTT   TGCCATGGGC

TGGCGATCCT   TCACCAATGT   CAACTCCAGG   ATGCTCTACT   TTGCCCCTGA

TCTGGTTTTC   AATGAGTACC   GCATGCACAA   ATCCCGGATG   TACAGCCAGT

GTGTCCGAAT   GAGGCACCTC   TCTCAAGAGT   TTGGATGGCT   CCAAATCACC

CCCCACGAAT   TCCTGTGCAT   GAAAGCGCTG   CTACTCTTCA   GCATTATTCC

AGTGGATGGG   CTGAAAAATC   AAAAATTCTT   TGATGAACTT   CGAATGAACT

ACATCAAGGA   ACTCGATCGT   ATCATTGCAT   GCAAAAGAAA   AAATCCCACA

TCCTGCTCAA   GGCGTTTCTA   CCAGCTCACC   AAGCTCCTGG   ACTCCGTGCA

GCCTATTGCG   AGAGAGCTGC   ATCAGTTCAC   TTTTGACCTG   CTAATCAAGT

CACACATGGT   GAGCGTGGAC   TTTCCGGAAA   TGATGGCAGA   GATCATCTCT

GTGCAAGTGC   CCAAGATCCT   TTCTGGGAAA   GTCAAGCCCA   TCTATTTCCA

CACCCAGTGA   AGCATTGGAA   ATCCCTATTT   CCTCACCCCA   GCTCATGCCC

CCTTTCAGAT   GTCTTCTGCC   TGTTA,
``` as set forth in SEQ ID NO: 1.

18. A DNA molecule of claim 17 which consists of nucleotide 423 to about nucleotide 3108 of SEQ ID NO: 1.

19. A DNA expression vector for expressing a *Macaca mulatta* AR protein wherein said expression vector comprises a DNA molecule of claim 17.

20. A DNA expression vector for expressing a *Macaca mulatta* AR protein wherein said expression vector comprises a DNA molecule of claim 18.

21. A host cell which expresses a recombinant *Macaca mulatta* AR protein wherein said host cell contains the expression vector of claim 19.

22. A host cell which expresses a recombinant *Macaca mulatta* AR protein wherein said host cell contains the expression vector of claim 20.

23. A process for expressing a *Macaca mulatta* AR protein in a recombinant host cell, comprising:

(a) transfecting the expression vector of claim 19 into a suitable host cell; and (b) culturing the host cells of step (a) under conditions which allow expression of said the *Macaca mulatta* AR protein from said expression vector.

24. The process of claim 23 wherein the host cell is a yeast host cell.

* * * * *